(12) United States Patent
Henry et al.

(10) Patent No.: US 9,873,786 B2
(45) Date of Patent: Jan. 23, 2018

(54) SYNTHETIC COMPOSITION AND COATING FOR CELL CULTURE

(75) Inventors: David Henry, Fontaine le Port (FR); Martial Hervy, Veneux les sablons (FR); Marylène Denise Madeleine Pécheul, Lieudit la brosse-Chaintreaux (FR); Corinne Walerack, Veneux les sablons (FR)

(73) Assignee: Corning Incorporated, Corning, NY (US)

( * ) Notice: Subject to any disclaimer, the term of this patent is extended or adjusted under 35 U.S.C. 154(b) by 1051 days.

(21) Appl. No.: 13/446,734

(22) Filed: Apr. 13, 2012

(65) Prior Publication Data

US 2012/0282697 A1    Nov. 8, 2012

(30) Foreign Application Priority Data

May 5, 2011    (WO) .................. PCT/IB2011/001493

(51) Int. Cl.
*C12N 5/00* (2006.01)
*C12N 11/08* (2006.01)
*C08L 33/14* (2006.01)

(52) U.S. Cl.
CPC ............ *C08L 33/14* (2013.01); *C12N 5/0068* (2013.01); *C12N 11/08* (2013.01); *C08L 2205/05* (2013.01); *C12N 2533/30* (2013.01); *C12N 2533/50* (2013.01)

(58) Field of Classification Search
CPC ...... C08L 33/14; C08L 89/00; C08L 2205/05; C12N 5/0068; C12N 11/08; C12N 2533/30; C12N 2533/50
See application file for complete search history.

(56) References Cited

U.S. PATENT DOCUMENTS

| | | | |
|---|---|---|---|
| 5,498,407 A | * | 3/1996 | Atlas ..................... A61K 8/027 424/401 |
| 5,512,329 A | | 4/1996 | Guire et al. |
| 6,121,027 A | | 9/2000 | Clapper et al. |
| 6,825,032 B2 | | 11/2004 | Dapron et al. |
| 7,030,213 B2 | | 4/2006 | Pierschbacher et al. |
| 7,045,366 B2 | | 5/2006 | Huang et al. |

(Continued)

FOREIGN PATENT DOCUMENTS

| | | | |
|---|---|---|---|
| EP | 2836560 | * | 2/2015 |
| JP | 2011-510655 A | | 4/2011 |

(Continued)

OTHER PUBLICATIONS

Marx, J. of Oral Maxillofacial Surgery, 2004, 62-489-96.*

(Continued)

*Primary Examiner* — Jeffrey E. Russel
(74) *Attorney, Agent, or Firm* — Susan S. Wilks

(57) ABSTRACT

A composition for forming a polymeric cell culture surface includes (i) a pre-polymer comprising a polymer backbone, a cationic moiety conjugated to the backbone, and a cross-linker moiety conjugated to the backbone; and (ii) a peptide-polymer comprising a polymer backbone and cell adhesive peptide conjugated to the backbone. Cross-linked coatings for cell culture that have a suitable amount of cell adhesive peptide and cationic moiety may be formed from the pre-polymer and peptide-polymer.

16 Claims, 13 Drawing Sheets

Component (i)

+

Component (ii)

(56) References Cited

U.S. PATENT DOCUMENTS

| | | | |
|---|---|---|---|
| 7,786,213 B2* | 8/2010 | Maynard | A61K 47/48176 525/54.1 |
| 8,530,236 B2 | 9/2013 | Fadeev et al. | |
| 2005/0106227 A1* | 5/2005 | Zalipsky | A61B 17/205 424/449 |
| 2009/0324685 A1* | 12/2009 | Falk | A61L 31/10 424/426 |

FOREIGN PATENT DOCUMENTS

| | | |
|---|---|---|
| WO | 2009099555 A2 | 8/2009 |
| WO | 2012014003 A1 | 2/2012 |

OTHER PUBLICATIONS

Marx, J. of Oral Maxillofacial Surgery, 2004, 62, 489-496.*
Mei, Nature Materials, 2010, 9, 768-778.*
Zara Melkoumian et al: "Synthetic peptide-acrylate surfaces for long-term self-renewal and cardiomyocyte differentiation of human embryonic stem cells", Nature Biotechnology, vol. 28, No. 6, Jun. 1, 2010, pp. 606-610, XP002636474.
Luis G Villa-Diaz et al: "Synthetic polymer coatings for long-term growth of human embryonic stem cells", Nature Biotechnology, vol. 28, No. 6, Jun. 1, 2010, pp. 581-583, XP55019660.
Kolhar P et al: "Synthetic surfaces for human embryonic stem cell culture", Journal of Biotechnology, vol. 146, No. 3, Apr. 1, 2010, pp. 143-146, XP026970393.
Brafman D A et al: "Long-term human pluripotent stem cell self-renewal on synthetic polymer surfaces", Biomaterials, vol. 31, No. 34, Dec. 1, 2010, pp. 9135-9144, XP027381078.
Japanese Office Action, Notice of Grounds for Rejection, dated Jun. 23, 2015, pp. 1-3., Japanese Application No. 2014-508877, Japanese Patent Office, Japan.
Besse and Moroder, "Synthesis of selenocysteine peptides and their oxidation to diselenide-bridged compounds", 1997, Journal of Peptide Science, vol. 3, 442-453.
Horak, et al., "Functional Polymer Hydrogel for Embryonic Stem Cell Support," published online Aug. 3, 2005 in Wiley Interscience.
Koide et al, "Synthetic study on selenocystine-containing peptides", 1993, Chem. Pharm. Bull. 41(3):502-6.
Koide et al., "Syntheses and biological activities of selenium analogs of alpha-rat atrial natriuretic peptide" 1993, Chem. Pharm. Bull. 41(9):1596-1600.
Sigrist et al., "Surface immobilization of biomolecules by light", Opticla engineering, Aug. 1995, vol. 34, No. 8, 2339.

* cited by examiner

SYNTHETIC COMPOSITION AND COATING FOR CELL CULTURE

CROSS-REFERENCE

This application claims the benefit of priority under 35 U.S.C. §365 of International Patent Application Serial No. PCT/IB2011/001493 filed on May 5, 2011 designating the United States of America the content of which is relied upon and incorporated herein by reference in its entirety.

FIELD

The present disclosure relates to cell culture, and more particularly to synthetic, chemically-defined coatings or surfaces and methods to prepare such coatings or surfaces.

SEQUENCE LISTING

This application contains a Sequence Listing electronically submitted via EFS-Web to the United States Patent and Trademark Office as text filed named "20110426_SP11-081_PCT_SEQUENCE_LISTING_ST25.txt" having a size of 9 kb and created on Apr. 22, 2011. Due to the electronic filing of the Sequence Listing, the electronically submitted Sequence Listing serves as both the paper copy required by 37 CFR §1.821(c) and the CRF required by §1.821(e). The information contained in the Sequence Listing is hereby incorporated herein by reference.

BACKGROUND

Therapeutic cells, cells which may be introduced into a human for the treatment of disease, are being developed. Examples of therapeutic cells include pluripotent stem cells such as human embryonic stem cells (hESCs) which have the ability to differentiate into any of the three germ layers, giving rise to any adult cell type in the human body. This property of stem cells provides a potential for developing new treatments for a number of serious cell degenerative diseases, such as diabetes, spinal chord injury, heart diseases and the like. However, there remain obstacles in the development of such hESC-based treatments.

Obtaining and maintaining adequate numbers of therapeutic cells in cell and tissue culture and ensuring that these cells do not change in unwanted ways during cell culture are important in developing and controlling therapeutic cell cultures. For example, stem cell cultures, such as hESC cell cultures, are typically seeded with a small number of cells from a cell bank or stock and then amplified in the undifferentiated state until differentiation is desired for a given therapeutic application. To accomplish this, the hESC or their differentiated cells are typically cultured in the presence of surfaces or media containing animal-derived components, such as feeder layers, serum, or Matrigel™ available from BD Biosciences, Franklin Lakes N.J. These animal-derived additions to the culture environment may expose the cells to potentially harmful viruses or other infectious agents which could be transferred to patients or which could compromise general culture and maintenance of the hESCs. In addition, such biological products are vulnerable to batch variation, immune response and limited shelf-life.

Recently, synthetic surfaces that are free of animal-derived components have been shown to be successful in the culture of stem cells, such hESCs, in chemically defined medium, addressing many of the issues that result from culturing cells in the presence of animal-derived components. However, such synthetic surfaces have been made with high concentrations of recombinant polypeptides, which can be expensive to manufacture. In addition, these synthetic surfaces may provide surfaces from which cells cannot readily be removed, often requiring long incubation times with proteolytic enzymes such as trypsin combined with cell scraping.

BRIEF SUMMARY

Among other things, the present disclosure describes synthetic coatings capable of supporting undifferentiated growth of stem cells in a chemically defined medium. In various embodiments, the concentration of peptide is lower than currently available synthetic surfaces for culture of stem cells and provide for cell harvesting under more mild conditions than the currently available synthetic surfaces. The coatings are formed from cross-linking a functionalized cell binding peptide polymer with a cationic cross-linker-functionalized pre-polymer having an amine group to form a cross-linked polymer. By controlling the ratio of the peptide polymer and the pre-polymer, the concentration of the cell binding polypeptide in the resulting cross-linked polymer can be adjusted. The ease with which the cells may be harvested from the surfaces may also be controlled by adjusting the ratio of the peptide polymer and the pre-polymer.

In various embodiments described herein, a composition for forming a polymeric cell culture surface includes (i) a pre-polymer comprising a polymer backbone, a cationic moiety conjugated to the backbone, and a cross-linker moiety conjugated to the backbone; and (ii) a peptide polymer comprising a polymer backbone and cell adhesive peptide conjugated to the backbone. Cross-linked coatings for cell culture that have a suitable amount of cell adhesive peptide and cationic moiety may be formed from the pre-polymer and the peptide polymer.

One or more embodiments of the cell culture articles, compositions, or methods described herein provide one or more advantages over prior cell culture articles, compositions, or methods for producing coated cell culture articles. For example, because the coating is fully synthetic, it does not suffer from batch variation, immune response, limited shelf-life and risk of exposure of the cells to potentially harmful viruses or other infectious agents which could be transferred to patients. In various embodiments, the coating is prepared using a concentration of cell adhesive peptide that is lower than other available or suggested synthetic surfaces. This lower peptide concentration may also facilitate cell harvesting by proteases such as trypsin. In various embodiments, the coating process is simple and allows for high throughput production of coated articles. For example, the coating process does not require in-situ polymerization and cross-linking may be done under air, eliminating a costly and complicated step of inert gas purge. Due to the simple coating process, the coating composition, or components thereof, may be provided as a kit for use in coating by an end user in almost any laboratory setting. These and other advantages will be readily understood from the following detailed description when read in conjunction with the accompanying drawings.

Figure 1:
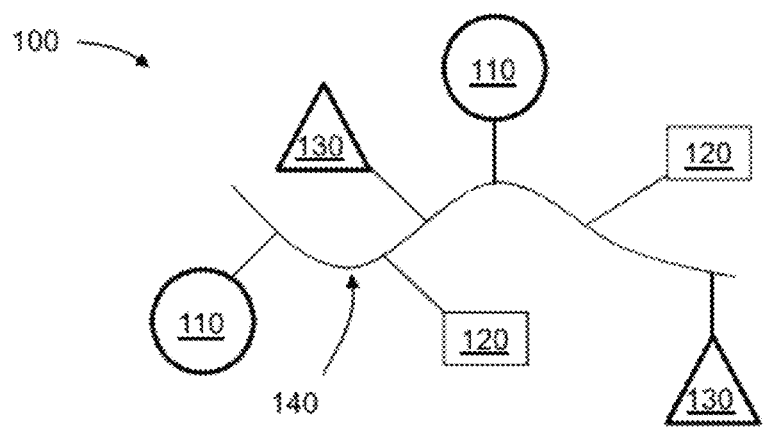
FIG. 1 is schematic drawing illustrating a generic embodiment of a component 1 pre-polymer in accordance with the teachings presented herein.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a composition, coating, article, method, or the like, means that the components of the composition, coating, article, method, or the like are limited to the enumerated components and any other components that do not materially affect the basic and novel characteristic(s) of the composition, coating, article, method, or the like.

As used herein, "pre-polymer" means a polymer or oligomer having reactive groups, which may be activatable reactive groups, that are capable of entering into further polymerization; e.g., through crosslinking. For example, a polymer having an activatable cross-linker group is a pre-polymer if the cross-linker group is activated and cross-linked to another polymer. For the purposes of this disclosure, the other polymer to which the pre-polymer having the activatable cross-linker cross links is not considered a pre-polymer unless it also has a reactive group. If the other polymer cross links with the pre-polymer through, e.g. non-specific proton adsorption induced by a reactive group of the pre-polymer, and does not cross-link due to specific reactive groups of the other polymer, then the other polymer is not a pre-polymer for purposes of this disclosure.

As used herein, "conjugated," as it relates to a monomer or polymer and a moiety such as a polypeptide or an activatable cross-linker group, means that the polypeptide or the activatable cross-linker group is covalently bound, either directly or indirectly (e.g., via a spacer) to the polymer or monomer.

As used herein, "monomer" means a compound capable of polymerizing with another monomer, (regardless of whether the "monomer" is of the same or different compound than the other monomer).

As used herein, a "(meth)acrylate monomer" means a methacrylate monomer or an acrylate monomer. As used herein "(meth)acrylamide monomer" means a methacrylamide or an acrylamide monomer. (Meth)acrylate and (meth) acrylamide monomers have at least one ethylenically unsaturated moiety. "Poly(meth)acrylate", as used herein, means a polymer formed from one or more monomers including at least one (meth)acrylate monomer. "Poly(meth) acrylamide", as used herein, means a polymer formed from one or more monomers including at least one (meth)acrylamide monomer.

As used herein, a "cationic" monomer, pre-polymer, polymer, or component or unit thereof, is a monomer, pre-polymer, polymer, or component or unit thereof that has a positive charge under cell culture conditions, such as at pH 7 to 7.7.

Polypeptide sequences are referred to herein by their one letter amino acid codes or by their three letter amino acid codes. These codes may be used interchangeably.

As used herein, "peptide" and "polypeptide" mean a sequence of amino acids that may be chemically synthesized or may be recombinantly derived, but that are not isolated as entire proteins from animal sources. For the purposes of this disclosure, peptides and polypeptides are not whole proteins. Peptides and polypeptides may include amino acid sequences that are fragments of proteins. For example peptides and polypeptides may include sequences known as cell adhesion sequences such as RGD. Polypeptides may be of any suitable length, such as between three and 30 amino acids in length. Polypeptides may be acetylated (e.g. Ac-LysGlyGly) or amidated (e.g.SerLysSer-$NH_2$) to protect them from being broken down by, for example, exopeptidases. It will be understood that these modifications are contemplated when a sequence is disclosed.

The present disclosure describes, inter alia, compositions and methods for coating cell culture articles by contacting the articles with a composition containing a cationic cross-linker functionalized pre-polymer ("component 1") and a cell binding peptide functionalized polymer ("component 2") and exposing the coated articles to conditions that cause cross-linking of the pre-polymer and the peptide polymer to produce a cell culture article with a cell attachment surface.

I. Component 1: Cationic Cross-Linker Functionalized Pre-Polymer

Component 1 is a pre-polymer that has a cross-linker moiety conjugated to a polymer backbone and has a cationic moiety conjugated to the polymer backbone. The cationic moiety is positively charged at cell culture pH, e.g. 7 to 7.7. The cross-linker moiety is capable of cross-linking the component 1 pre-polymer to the component 2 peptide containing polymer and, in some embodiments, a surface of a cell culture article upon exposure to, for example, electromagnetic radiation such as UV light. The component 1 pre-polymer is preferably prepared by polymerization of at least one cationic monomer and at least one cross-linker containing monomer. Alternatively, cationic groups or photoreactive groups may be conjugated to a polymer backbone comprising reactive groups.

In various embodiments, the component 1 pre-polymer further includes a hydrophilic component. For example and with reference to FIG. 1, a schematic component 1 pre-polymer 100 is shown. The pre-polymer 100 has a polymer backbone 140 and cross-linker moieties 110, cationic moieties 120, and hydrophilic moieties 130 conjugated to the backbone 140. In many embodiments, the pre-polymer 100 is cross-link free or substantially cross-link free, as some cross-linking due to incidental activation of some of the cross-linker moieties 110 may occur.

Figure 2:
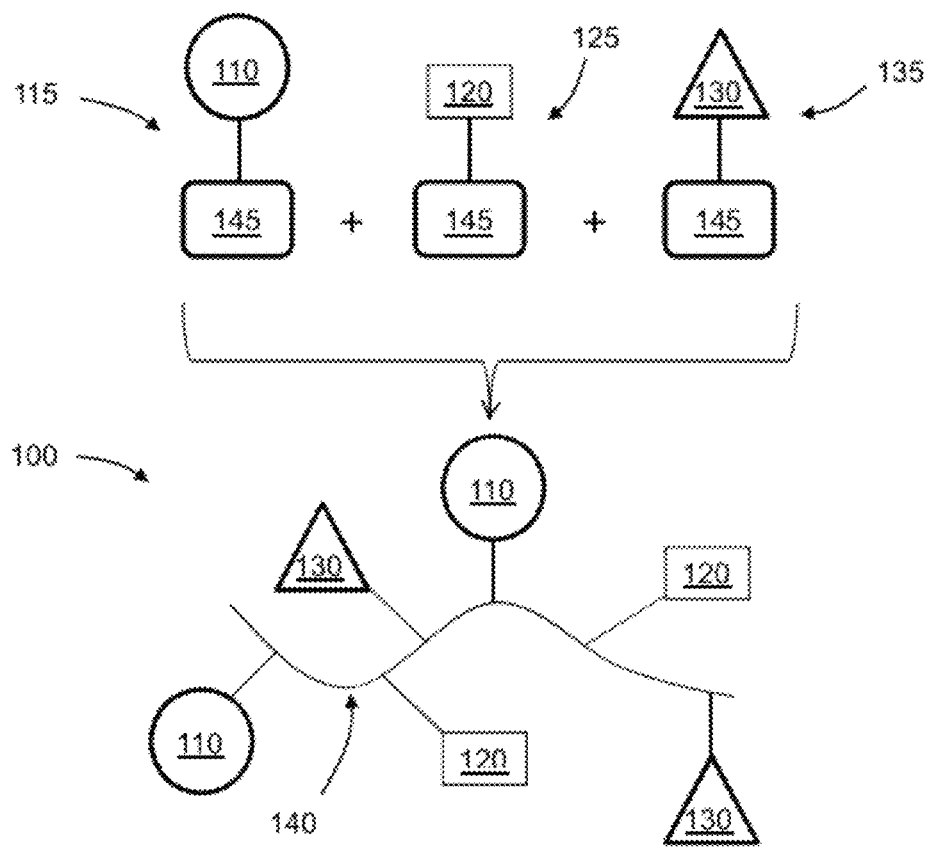
FIG. 2 is a schematic drawing showing a reaction scheme for producing a generic embodiment of a component 1 pre-polymer in accordance with embodiments presented herein.

The component 1 pre-polymer 100 may be formed using any suitable process. For example and with reference to FIG. 2, the pre-polymer 100 may formed from polymerization of a mixture of monomers comprising a polymerization moiety 145 conjugated to the cross-linker moiety 110 ("cross-linker monomer" 115), a polymerization moiety 145 conjugated to the cationic moiety 120 ("cationic monomer" 125), and a polymerization moiety 145 conjugated to the hydrophilic moiety 130 ("hydrophilic monomer" 135). It will be understood that the polymerization moiety 145 may be the same or different.

In embodiments, the polymerization moieties 145 used to form the pre-polymers contain an ethylenically unsaturated group, such as (meth)acrylates, (meth)acrylamides, maleimides, fumurates, vinylsulfones, or the like. The cross-linker moiety 110, the cationic moiety 120, or the hydrophilic moiety 130 may be conjugated to any suitable polymerization moiety or may be a part of known monomers. Rather than being conjugated to a polymerization moiety, the cross-linker moiety 110, the cationic moiety 120, or the hydrophilic moiety 130 may be conjugated to an existing polymer by, for example, covalently coupling the cross-linker moiety to the side groups of a polymer chain to introduce the cross-linker functionality, the cationic functionality, or the hydrophilic functionality.

A. Cross-Linker Moiety

Any suitable cross-linker moiety 110 may be used to form a cross-linker monomer 115 or for conjugating to an existing polymer. The cross-linker moiety 110 may be a photoreactive moiety or a thermally reactive moiety. For example, the cross-linker moiety may be an $\alpha,\beta$ unsaturated ketone photo-reactive group. A photo-reactive group is a molecule or moiety that forms a highly reactive species upon exposure to light. Examples of photo-reactive groups include aryl azides, diazarenes, beta carbonyldiazo and benzophenones, acetophenones and derivatives thereof. Reactive species include nitrenes, carbenes and radicals. The reactive species are generally capable of forming covalent bonds. For example, in embodiments the photosensitive moiety is a benzophenone containing moiety, substituted arylazide containing moiety or trifluoromethylaryldiazirine containing moiety.

In embodiments, the cross-linker monomer 115 is N-(3-methacrylamidopropyl)-4-benzoylbenzamide. Other suitable cross-linker monomers having polymerizable benzophenone include 2-acryloxy-5-methyl benzophenone, 4'-dimethylamino-2-acryloxy-5-methyl benzophenone, and 4'-dimethylamino-2-(β-acryloxyethyl)oxy-5-methyl benzophenone, 4-benzophenone methoxyl methacrylate, 4-vinyl-4'-methoxy benzophenone, 2-methyl-4'-vinyl benzophenone and 4-vinyl benzophenone, 4-[(4-maleimido)phenoxy]benzophenone, 4-[(4-maleimido)thiophenyl]benzophenone, acrylic acid 4-[3-(4-benzoyl-phenoxy)-2-hydroxypropoxy] butyl ester.

B. Cationic Moiety

Any suitable cationic moiety 120 may be used to form a cationic monomer 125 or for conjugating to an existing polymer. In embodiments, the cationic moiety 120 comprises an amine group, such as a primary, secondary or tertiary amino group. The cationic group may be also a quaternary amine made by quaternization of the parent tertiary amine. In various embodiments, the cationic moiety 120 is a tertiary alkylamine or a tertiary alkanolamine, such as a mono- or di-substituted C1-C4 alkylamine or a mono- or di-substituted C1-C4 alkanolamine.

In various embodiments, a cationic monomer 125 is a monoalkylaminoalkyl or dialkylaminoalkyl (meth)acrylates. Examples of monoalkylaminoalkyl or dialkylaminoalkyl (meth)acrylates that may be used include N,N-dimethylaminoethyl-, N,N-diethylaminoethyl-, N,N-dipropylaminoethyl (meth)acrylate or N-tert-butylaminoethyl (meth)acrylate. Alternatively, in place of these ester monomers, corresponding reaction products of glycidyl (meth)acrylate and secondary alkylamines or alkanolamines may be used. In various embodiments, the cationic monomer 125 is 2-(dimethylamino)ethyl methacrylate (DMEMA).

C. Hydrophilic Moiety

Any suitable hydrophilic moiety 130 may be used to form a hydrophilic monomer 135 or for conjugating to an existing polymer. The hydrophilic moiety 130 or monomer 135 may be negatively charged at cell culture pH or uncharged at cell culture pH. In many embodiments, the hydrophilic moiety 130 or monomer 135 is uncharged at cell culture pH. The hydrophilic moiety 130 or monomer 135 may be employed to adjust the charge density of the component 1 pre-polymer 100 or provide a hydrogel behaviour to the resulting polymer.

In various embodiments, the hydrophilic monomer 135 is a (meth)acrylate monomer of Formula (I):

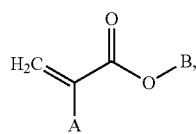

(I)

where A is H or methyl, and where B is H, C1-C6 straight or branched chain alcohol or hydroxyl-terminal ether, or C1-C6 straight or branched chain alkyl substituted with a carboxyl group (—COOH). In some embodiments, B is C1-C4 straight or branched chain alcohol. In some embodiments, B is straight or branched chain C1-C3 substituted with a carboxyl group. By way of example, 2-carboxyethyl methacrylate, 2-carboxyethyl acrylate, acrylic acid, methacrylic acid, hydroxypropyl methacrylate, 2-hydroxyethyl methacrylate (HEMA), 2-hydroxyethyl acrylate, glycerol methacrylate, hydroxypropyl acrylate, 4-hydroxybutyl acrylate, or the like may be employed.

In various embodiments, the hydrophilic monomer 135 is a (meth)acrylamide monomer of Formula (II):

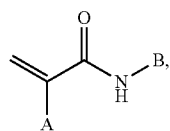

(II)

where A is hydrogen or methyl, and where B is H, C1-C6 straight or branched chain alcohol or hydroxyl-terminal ether, or C1-C6 straight or branched chain alkyl substituted with a carboxyl group (—COOH). In some embodiments, B is straight or branched chain C1-C3 substituted with a carboxyl group. In some embodiments, B is C1-C4 straight or branched chain alcohol. By way of example, 2-carboxyethyl acrylamide, acrylamido glycolic acid, N-(hydroxymethyl)acrylamide, N-[Tris(hydroxymethyl)methyl]acrylamide, 3-acryloylamino-1-propanol, N-acrylamidoethoxyethanol, N-hydroxyethyl acrylamide, or the like, may be used.

D. Synthesis of Component 1 Pre-polymer

As discussed above, component 1 pre-polymer 100 may be synthesized in any suitable manner, such as by conjugating appropriate moieties to a homopolymer or copolymer or by polymerizing a mixture of monomers having the appropriate moieties conjugated to the monomers.

In a preferred embodiment, the component 1 pre-polymer 100 is synthesized by polymerizing a mixture comprising a cross-linker monomer 115, a cationic monomer 125 and a hydrophilic monomer 135. The molar ratios of the various monomers may be varied as appropriate. It will be understood that higher concentrations of the cross-linker monomer 115 will ultimately increase the cross-linking with the component 2 peptide polymer (as discussed below in more detail). It will be further understood that higher concentrations of the cationic monomer 125 will increase the charge density of the pre-polymer 100. The concentration of the hydrophilic monomer 135 may be varied to control the cross-link density and charge density, as desired, and may impart hydrogel properties to the pre-polymer 100.

Any suitable molar percentages of the cross-linker monomer 115, cationic monomer 125 and hydrophilic monomer 135 may be used. In embodiments, the cross-linker monomer 115 constitutes between 1% (molar percent) and 20% (molar percent) of the mixture of monomers used to form the component 1 pre-polymer 100. For example, the cross-linker monomer 115 constitutes between 1% and 10% of the mixture of monomers used to form the component 1 pre-polymer 100.

In embodiments, the cationic monomer 125 constitutes between 1% (molar percent) and 50% (molar percent) of the mixture of monomers used to form the component 1 pre-polymer 100. For example, the cationic monomer 125 constitutes between 10% and 30% of the mixture of monomers used to form the component 1 pre-polymer 100.

In embodiments, the hydrophilic monomer 135 constitutes between 98% (molar percent) and 30% (molar percent) of the mixture of monomers used to form the component 1 pre-polymer 100. For example, the hydrophilic monomer 135 constitutes between 89% and 60% of the mixture of monomers used to form the component 1 pre-polymer 100.

Once the appropriate monomers in the appropriate amounts are selected, the polymer may be formed via polymerization reaction. In addition to the monomers that form the polymer, a composition may include one or more additional compounds such as surfactants, wetting agents, photoinitiators, thermal initiators, catalysts, and activators.

Any suitable polymerization initiator may be employed. One of skill in the art will readily be able to select a suitable initiator, e.g. a radical initiator or a cationic initiator, suitable for use with the monomers. In various embodiments, UV light is used to generate free radical monomers to initiate chain polymerization. Examples of polymerization initiators include organic peroxides, azo compounds, quinones, nitroso compounds, acyl halides, hydrazones, mercapto compounds, pyrylium compounds, imidazoles, chlorotriazines, benzoin, benzoin alkyl ethers, diketones, phenones, or mixtures thereof. Examples of suitable commercially available, ultraviolet-activated and visible light-activated photoinitiators have tradenames such as IRGACURE 651, IRGACURE 184, IRGACURE 369, IRGACURE 819, DAROCUR 4265 and DAROCUR 1173 commercially available from Ciba Specialty Chemicals, Tarrytown, N.Y.

and LUCIRIN TPO and LUCIRIN TPO-L commercially available from BASF (Charlotte, N.C.)

A photosensitizer may also be included in a suitable initiator system. Representative photosensitizers have carbonyl groups or tertiary amino groups or mixtures thereof. Photosensitizers having a carbonyl groups include benzophenone, acetophenone, benzil, benzaldehyde, o-chlorobenzaldehyde, xanthone, thioxanthone, 9,10-anthraquinone, and other aromatic ketones. Photosensitizers having tertiary amines include methyldiethanolamine, ethyldiethanolamine, triethanolamine, phenylmethyl-ethanolamine, and dimethylaminoethylbenzoate. Commercially available photosensitizers include QUANTICURE ITX, QUANTICURE QTX, QUANTICURE PTX, QUANTICURE EPD from Biddle Sawyer Corp.

In general, the amount of photosensitizer or photoinitiator system may vary from about 0.01 to 10% by weight.

Examples of cationic initiators that may be employed include salts of onium cations, such as arylsulfonium salts, as well as organometallic salts such as ion arene systems.

Examples of free radical initiators that may be employed include azo-type initiators such as 2-2'-azobis(dimethylvaleronitrile), azobis(isobutyronitrile), azobis(cyclohexanenitrite), azobis(methyl-butyronitrile), and the like, peroxide initiators such as benzoyl peroxide, lauroyl peroxide, methyl ethyl ketone peroxide, isopropyl peroxy-carbonate, 2,5-dienethyl-2,5-bas(2-ethylhexanoyl-peroxy)hexane, di-tert-butyl peroxide, cumene hydroperoxide, dichlorobenzoyl peroxide, potassium persulfate, ammonium persulfate, sodium bisulfate, combination of potassium persulfate, sodium bisulfate and the like, and mixtures thereof. Of course, any other suitable free radical initiators may be employed. An effective quantity of an initiator is generally within the range of from about 0.1 percent to about 15 percent by weight of the reaction mixture, such as from 0.1 percent to about 10 percent by weight or from about 0.1 percent to about 8 percent by weight of the reaction mixture.

In various embodiments, one or more monomers are diluted prior to undergoing polymerization.

The pre-polymer 100 resulting from the polymerization reaction may have any suitable molecular weight. In various embodiments, the pre-polymer 100 has an average molecular weight (Mw) of between 10,000 and 1000,000 Daltons, such as between 10,000 and 250,000 Daltons. One of skill in the art will understand that the amount of initiator, reaction time, reaction temperature, and the like may be varied to adjust the molecular weight of the resulting polymer.

(Meth)acrylate monomers, (meth)acrylamide monomers, or other suitable monomers may be synthesized as known in the art or obtained from a commercial vendor, such as Polysciences, Inc., Sigma Aldrich, Inc., and Sartomer, Inc.

Figure 3:
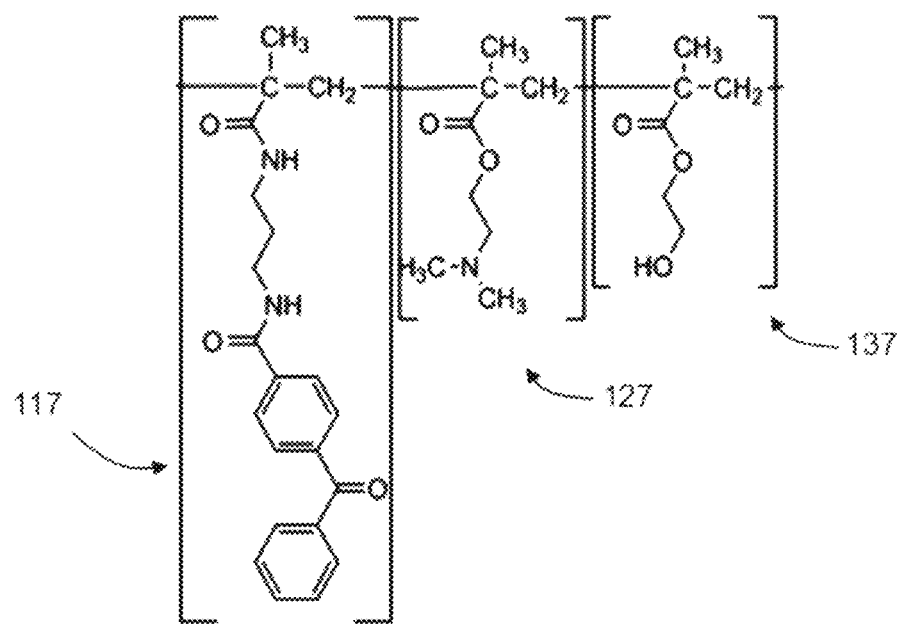
FIG. 3 is a schematic drawing illustrating some specific components of a component pre-polymer in accordance with embodiments presented herein.

In embodiments, the component pre-polymer 100 is referred to as "Photo-DMAE". For the purposes of this disclosure, "Photo-DMAE" is a pre-polymer formed from polymerization of a mixture of monomers consisting of N-(3-methacrylamidopropyl)-4-benzoylbenzamide, DMEMA and HEMA, e.g. as shown in FIG. 3, where 117 is derived from the cross-linker monomer [N-(3-methacrylamidopropyl)-4-benzoylbenzamide], 127 is derived from the cationic monomer (DMEMA), and 137 is derived from the hydrophilic monomer (HEMA).

II. Component 2: Peptide Functionalized Polymer

Component 2 is a polymer that has a polypeptide conjugated to a polymer backbone. The polypeptide may be conjugated to the polymer in any suitable manner. In some embodiments a monomer is derivatized to include the polypeptide and, thus, the polypeptide is incorporated into the polymer as it is being formed. In some embodiments, the polypeptide is grafted to the polymer after the polymer is formed.

Figure 4:
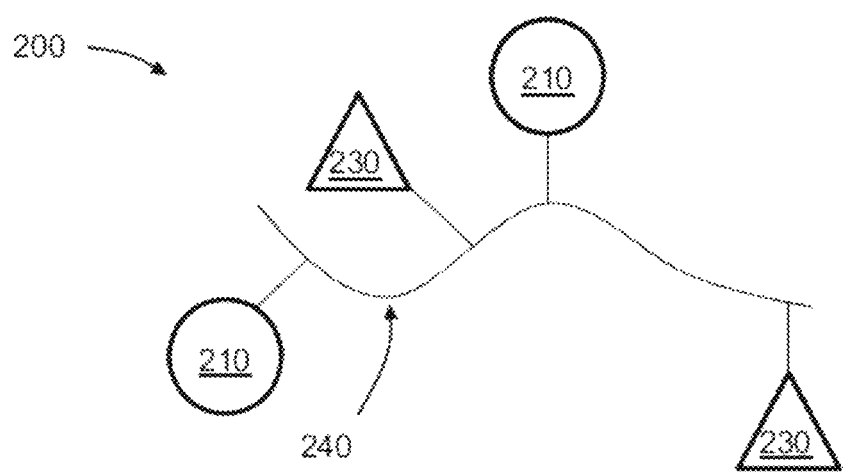
FIG. 4 is schematic drawing illustrating a generic embodiment of a component 2 polymer in accordance with the teachings presented herein.

In various embodiments, the component 2 polymer further includes a hydrophilic component. For example and with reference to FIG. 4, a schematic component 2 polymer 200 is shown. The polymer 200 has a polymer backbone 240 and cell binding peptide moieties 210 and hydrophilic moieties 230 conjugated to the backbone 240. In many embodiments, the polymer 200 is cross-link free or substantially cross-link free.

The component 2 polymer 200 may be formed using any suitable process. For example and with reference to FIG. 5, the polymer 200 may formed from polymerization of a mixture of monomers comprising a polymerization moiety 245 conjugated to the peptide moiety 210 ("peptide monomer" 215) and a polymerization moiety 245 conjugated to the hydrophilic moiety 230 ("hydrophilic monomer" 235). It will be understood that the polymerization moieties 245 may be the same or different. The polymerization moieties 245 or hydrophilic monomers 235 may be as described above for the polymerization moieties 145 or hydrophilic monomers 145 with regard to the component 1 pre-polymer.

Any suitable molar ratio of peptide monomer 215 to hydrophilic monomer 245 may be used. In various embodiments, a mixture of monomers for used in forming the component 2 pre-polymer 200 consists of a peptide monomer 215 and a hydrophilic monomer 235, where the molar ratio of the peptide monomer 215 to the hydrophilic monomer 235 is between 0.03 to 1 and 0.9 to 1, for example between 0.06 to 1 and 0.2 to 1. It will be understood that the concentration of the hydrophilic monomer 235 may be varied to control the concentration of the peptide in the resulting pre-polymer 200 and to impart desired hydrogel properties to the resulting pre-polymer 200.

In embodiments, the peptide monomer 215 peptide is described by formula 1:

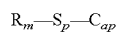  Formula 1

In embodiments, $R_m$ is a polymerization moiety, an α,β-unsaturated group or ethylenically unsaturated group which includes acrylate, methacrylate, acrylamide, methyacrylamide, maleimide or a fumarate, which is capable of polymerizing in the presence of an external energy source. "m" is an integer greater than or equal to 1. In embodiments, the functionalized peptide has a polymerization moiety $R_m$ which may be a photopolymerizable moiety or a thermal polymerizable moiety.

In embodiments, $S_p$ is a spacer. In embodiments, $S_p$ may be a polyalkylene oxide including for example polyethylene glycol (PEG) or polypropylene glycol (PPG) which are represented by the formula $(O-CH_2CHR')_{m2}$ where R' is H or $CH_3$ and m2 is an integer from 0 to 200, such as 0 to 100 or 0 to 20. The spacer may be a hydrophilic spacer, for example, polyethelene oxide (PEO). In embodiments, the spacer is $PEO_4$. In embodiments, relatively short chains of polyalkylene oxide are desirable. For example, in embodiments, $S_p$ may be $PEG_2$, $PEG_4$, $PEG_6$, $PEG_8$, $PEG_{10}$, $PEG_{12}$ or $PPG_2$, $PPG_4$, $PPG_6$, $PPG_8$, $PPG_{10}$, $PPG_{12}$ or $PPG_{20}$. In embodiments, the spacer is a polyethylene oxide with 20 or fewer repeating units (i.e. $PEG_4$, $PEG_6$, $PEG_8$, $PEG_{10}$, $PEG_{12}$, $PEG_{14}$, $PEG_{16}$, $PEG_{18}$ or $PEG_{20}$). In embodiments $S_p$ is PPG or PEG having a functional group. For example, the PEG or PPG spacer may have a maleimide, thiol, amine, silane, aldehyde, epoxide, isocyanate, acrylate or carboxyl group. In embodiments the PEG spacer is a Jeffamine, a PEG having an amine functional group. In additional embodiments, the PEG or PPG may be branched. For example the branched PEG or PPO may be a Y-branched or star-PEG or PPG. In embodiments these branched PEG or PPO spacers may allow multiple peptides to be conjugated to a base material through a single functional peptide.

Once a cell culture surface is formed (discussed below in more detail), the spacer may act to extend the peptide ($C_{ap}$) away from the cell culture surface, making the peptide more accessible to cells in culture, and improving the efficiency of the surface for cell culture. In addition, hydrophilic spacers may act to repel proteins, preventing non-specific absorption of cells or proteins to the functionalized peptide. In embodiments, the use of a cell adhesive peptide with a spacer such as PEO (polyethylene oxide) in preparing cell culture articles allows for the preparation of such articles using a lower overall concentration of adhesive peptide.

In embodiments, $S_p$ may be an amino acid $Xaa_n$ where Xaa is independently any amino acid and n is an integer from 0 to 30, from 0 to 10, from 0 to 6 or from 0 to 3. For example, in embodiments, $S_p$ may be an amino acid $Xaa_n$ where Xaa is G and where n=1 to 20, or $S_p$ may be an amino acid $Xaa_n$ where Xaa is K and n=1 to 20, or $S_p$ may be an amino acid $Xaa_n$ where Xaa is D and n=1 to 20, or $S_p$ may be an amino acid $Xaa_n$ where Xaa is E and n=1 to 20. In embodiment, spacer $S_p$ may be a three amino acid sequence such as LysGlyGly or LysTyrGly. In embodiments, $Xaa_n$ is a series of the same amino acid. In embodiments, the spacer $S_p$ may be combinations of $Xaa_n$ and polyethylene or polypropylene oxide. $Xaa_n$ may comprise a hydrophilic amino acid such as lysine, glycine, glutamic acid, aspartic acid or arginine amino acid. In embodiments, $Xaa_n$ may have a terminal lysine or arginine. Or, in embodiments, the spacer $S_p$ may comprise polyethylene oxide spacer and amino acid spacer in any combination. In embodiments, $S_p$ may be a hydrophobic spacer such as palmitic acid, stearic acid, lauric acid or hexaethylene diamine. In embodiments, $S_p$ may be carboxyethyl methacrylate.

The polymerization moiety may attach to the spacer, $S_p$ through the polyethylene oxide, through the side chain of an amino acid such as lysine or at the N-terminus of the amino acid. Amino acid $Xaa_n$ may be acetylated and/or amidated to protect it from degradation. However, if $Xaa_n$ is acetylated, the polymerization moiety cannot be bound to $Xaa_n$ through the N-terminus of the amino acid. For example, a methacrylic acid may be bound to a lysine amino acid through the side chain of the lysine amino acid where $S_p$ is $Xaa_n$, Xaa is lysine, n=1, and $R_m$ is methacrylic acid.

In embodiments, the spacer $S_p$ is $Xaa_n$ and $Xaa_n$ has a terminal lysine. In embodiments, $Xaa_n$ may be bound to a polymerization moiety $R_m$. For example, $Xaa_n$ may be (MAA)LysGlyGly or (MAA)LysTyrGly, where MAA is the polymerization moiety methacrylic acid (MAA) bound to $Xaa_n$ through the side chain of the terminal lysine amino acid. In additional embodiments, the polymerization moiety may be bound to the N-terminus of the $Xaa_n$ amino acid or amino acid chain, if the N-terminus is not acetylated. Each functionalized peptide has at least one polymerization moiety, and may have more than one.

$C_{ap}$ is a peptide or polypeptide having a cell adhesive or cell binding sequence. In embodiments the cell adhesive or cell binding sequence is RGD.

In embodiments, the component 2 polymer 200 may be formed from the polymerization product of peptide monomer 215, as described above. In additional embodiments, the component 2 polymer 200 may be formed from the polymerization product of peptide monomers 215 copolymerized in any form, for example as random copolymers or block copolymers, with additional monomers such as hydrophilic monomers 245. The use of multiple monomers to produce the polymer allows one to more readily tune the properties of the resulting polymer as desired, regardless of whether the polypeptide is incorporated into the polymer as the polymer is formed. In addition, the use of an additional monomer, such as a hydrophilic monomer 235, allows for the concentration of peptide to be controlled.

In embodiments, these additional monomers (in addition to the peptide monomer 215) are ethylenically unsaturated monomers, including, for example, (meth)acrylate monomers include lower alkyl, i.e. $C_1$ to $C_{20}$alkyl, (meth)acrylates, e.g. methyl (meth)acrylate, ethyl (meth)acrylate, propyl (meth)acrylate, n-butyl (meth)acrylate, iso-butyl (meth)acrylate, t-butyl (meth)acrylate, 2-ethyl hexyl (meth)acrylate. octyl (meth)acrylate or dodecyl (meth)acrylate. Additionally, cyclic alkyl monomeric species may be used such as cyclohexyl (meth)acrylate, isobornyl (meth)acrylate and dicyclopentenyl (meth)acrylate. Functional monomers such as methacrylic acid and acrylic acid, hydroxy alkyl methacrylates such as hydroxy ethyl (meth)acrylate (HEMA), hydroxypropyl (meth)acrylate and hydroxybutyl (meth)acrylate, glycidyl (meth)acrylate, dialkyl aminoalkyl (meth)acrylates such as dimethyl aminoethyl (meth)acrylate, diethyl aminoethyl (meth)acrylate, dimethyl aminopropyl (meth)acrylate and diethyl aminopropyl (meth)acrylate. By (meth)acrylate, we mean that either the methacrylate or the analogous acrylate may be used. In embodiments, the additional monomers may be non-ionic. In embodiments, the additional monomers may be hydrophilic.

Figure 6:
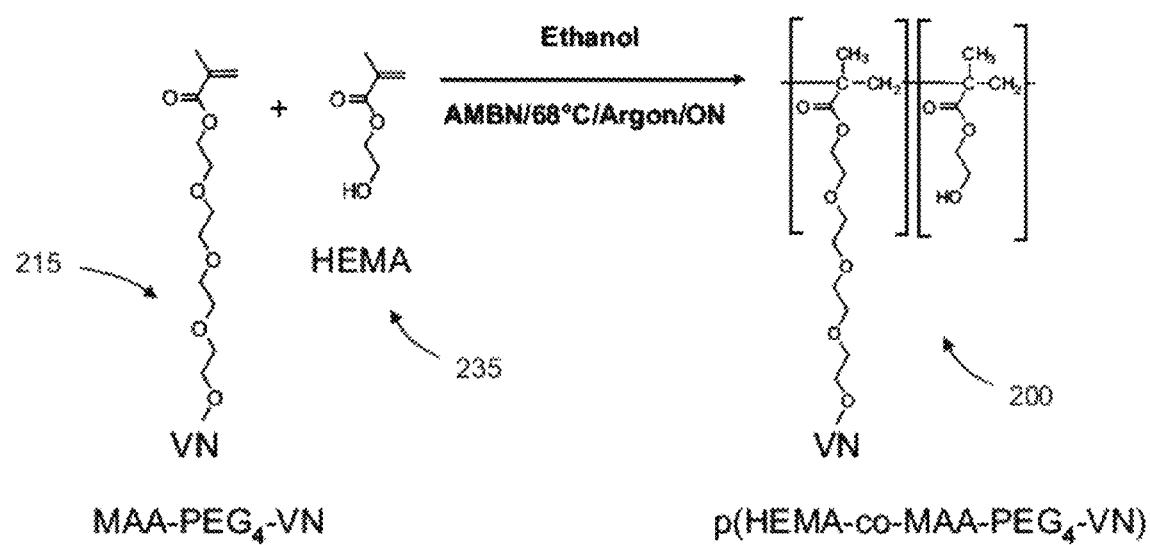
FIG. 6 is a schematic drawing of a reaction scheme for making a poly(HEMA-co-MAA-PEG4-VN) copolymer having a conjugated cell adhesive polypeptide.

FIG. 6 shows a reaction scheme for making poly(HEMA-co-MAA-PEG$_4$-VN), an embodiment of the component 2 polymer 200. As shown in FIG. 6, the peptide monomer 215 has a PEG$_4$ spacer and a methacrylic acid (MAA) polymerization moiety. Referring back to Formula 1: $R_m$—$S_p$—$C_{ap}$, according to the embodiment illustrated in FIG. 6, $R_m$ is MAA, Sp is PEG$_4$ and Cap is VN, a vitronectin sequence, which may be any of the sequences shown in Table 1 labeled VN, containing an RGD sequence. As shown in FIG. 6, a MAA-PEG$_4$-VN functionalized peptide is reacted with a hydrophilic ethylenically unsaturated monomer 235, in this case HEMA, in the presence of ethanol, a thermal initiator or a at 68° C. under argon or $N_2$, to form an embodiment of the component 2 polymer 200, HEMA-co-MAA-PEG$_4$-VN (further detail is provided in the Examples that follow).

In various embodiments, a polypeptide is grafted to a polymer that has already been formed. Preferably, polypeptide includes an amino acid capable of conjugating to a pendant reactive group of the polymer. Examples of reactive groups that the polymer may have for reaction with a polypeptide include maleimide, glycidyl, isocyanate, isothiocyanate, activated esters, activated carbonates, anhydride, and the like. By way of example, any native or biomimetic amino acid having functionality that enables nucleophilic addition; e.g. via amide bond formation, may be included in polypeptide for purposes of conjugating to the polypeptide having a suitable reactive group. Lysine, homolysine, ornithine, diaminopropionic acid, and diaminobutanoic acid are examples of amino acids having suitable properties for conjugation to a reactive group of the polymer, such as carboxyl group. In addition, the N-terminal alpha amine of a polypeptide may be used to conjugate to the carboxyl group, if the N-terminal amine is not capped. In various embodiments, the amino acid of polypeptide that conjugates with the polymer is at the carboxy terminal position or the amino terminal position of the polypeptide.

A polypeptide may be conjugated to the polymer via any suitable technique. A polypeptide may be conjugated to a polymer via an amino terminal amino acid, carboxy terminal amino acid, or an internal amino acid. One suitable technique involves 1-ethyl-3-[3-dimethylaminopropyl] carbodiimide hydrochloride (EDC)/N-hydroxysuccinimide (NHS) chemistry, as generally known in the art. EDC and NHS or N-hydroxysulfosuccinimide (sulfo-NHS) can react with free carboxyl groups of the polymer to produce amine reactive NHS esters. EDC reacts with a carboxyl group of the polymer to produce an amine-reactive O-acylisourea intermediate that is susceptible to hydrolysis. The addition of NHS or sulfo-NHS stabilizes the amine-reactive O-acylisourea intermediate by converting it to an amine reactive NHS or sulfo-NHS ester, allowing for a two-step procedure. Following activation of the polymer, the polypeptide may then be added and the terminal amine of the polypeptide can react with the amine reactive ester to form a stable amide bond, thus conjugating the polypeptide to the swellable (meth)acrylate layer. When EDC/NHS chemistry is employed to conjugate a polypeptide to the polymer, the N-terminal amino acid is preferably an amine containing amino acid such as lysine, ornithine, diaminobutyric acid, or diaminopropionic acid. Of course, any acceptable nucleophile may be employed, such as hydroxylamines, hydrazines, hydroxyls, and the like.

EDC/NHS chemistry results in a zero length conjugation of polypeptide to microcarrier. Spacers (Sp), such as those described above and having a terminal amine may be added to the N-terminal amino acid of polypeptide. When adding a spacer (Sp) to the N-terminal amino acid, the spacer (Sp) is preferably a N-PG-amido-spacer where PG is a protecting group such as the Fmoc group, the BOC group, the CBZ group or any other group amenable to peptide synthesis.

In some embodiments where the polypeptide is conjugated to a polymer that has already formed, the polymer has backbone formed from a plurality of ethylenically unsaturated monomers, where one of the ethylinically unsaturated monomers has a carboxyl functional group. Those of skill in the art will recognize that a carboxyl functional group may be incorporated into the ethylenically unsaturated monomers listed above, where there are suitable functional groups, without undue experimentation. An example of a monomer having a carboxyl functional group is 2-carboxyethylacrylate (CEA), although many other carboxyl-group containing monomers may be used. In embodiments, the component 2 polymer 200 is formed from one or more ethylenically unsaturated monomer not having a carboxyl group, which may be a hydrophilic monomer (e.g., as discussed above) and from one or more ethylenically unsaturated monomer not having a carboxyl group. The peptide may be conjugated to the polymer backbone via the carboxyl functional group as described above.

Regardless of whether the polypeptide is conjugated to a polymer already formed or incorporated into a polymer as it is being formed, the peptide is a cell adhesive peptide or cell adhesive polypeptide (which terms are interchangeable) ($C_{ap}$). The cell adhesive polypeptide has a cell binding or cell adhesive sequence which may, for example, be an integrin binding sequence or an R-G-D sequence. In embodiments, the cell adhesive peptide is a sequence of amino acids found in vitronectin, laminin, bone sialoprotein, collagen, or fibronectin. For the purposes of this disclosure, peptide or polypeptide is an amino acid sequence that may be chemically synthesized or made by recombinant methods. However, for the purposes of this disclosure, peptide or polypeptide is a fragment of a protein, and not a complete protein. In addition, peptide or polypeptide is not isolated from an animal source. In embodiments, peptide or polypeptide may include an amino acid sequence of $Yaa_l$ProGlnValThrArgGlyAspValPheThrMetPro (SEQ ID NO:32), a vitronectin peptide sequence where l is an integer from 0 to 3 and where Yaa may be any amino acid or may include, for example, lysine of which the terminal amino acid must be lysine or arginine to accommodate attachment of a polymerizable group. In embodiments, the peptide or polypeptide may be cyclic. For example RGDYK(SEQ ID NO:33) may be cyclic c(RGDyK).

Examples of peptides that may be used in embodiments are listed in Table 1.

TABLE 1

| Sequence | Source |
| --- | --- |
| KGGGQKCIVQTTSWSQCSKS (SEQ ID NO: 1) | Cyr61 res 224-240 |
| GGGQKCIVQTTSWSQCSKS (SEQ ID NO: 2) | Cyr61 res 224-240 |
| KYGLALERKDHSG (SEQ ID NO: 3) | TSP1 res 87-96 |
| YGLALERKDHSG (SEQ ID NO: 4) | TSP1 res 87-96 |
| KGGSINNNRWHSIYITRFGNMGS (SEQ ID NO: 5) | mLMα1 res 2179-2198 |
| GGSINNNRWHSIYITRFGNMGS (SEQ ID NO: 6) | mLMα1 res 2179-2198 |
| KGGTWYKIAFQRNRK (SEQ ID NO: 7) | mLMα1 res 2370-2381 |
| GGTWYKIAFQRNRK (SEQ ID NO: 8) | mLMα1 res 2370-2381 |
| KGGTSIKIRGTYSER (SEQ ID NO: 9) | mLMγ1 res 650-261 |
| GGTSIKIRGTYSER (SEQ ID NO: 10) | mLMγ1 res 650-261 |
| KYGTDIRVTLNRLNTF (SEQ ID NO: 11) | mLMγ1 res 245-257 |
| YGTDIRVTLNRLNTF (SEQ ID NO: 12) | mLMγ1 res 245-257 |
| KYGSETTVKYIFRLHE (SEQ ID NO: 13) | mLMγ1 res 615-627 |
| YGSETTVKYIFRLHE (SEQ ID NO: 14) | mLMγ1 res 615-627 |
| KYGKAFDITYVRLKF (SEQ ID NO: 15) | mLMγ1 res 139-150 |
| YGKAFDITYVRLKF (SEQ ID NO: 16) | mLMγ1 res 139-150 |
| KYGAASIKVAVSADR (SEQ ID NO: 17) | mLMα1 res2122-2132 |
| YGAASIKVAVSADR (SEQ ID NO: 18) | mLMα1 res2122-2132 |
| CGGNGEPRGDTYRAY (SEQ ID NO: 19) | BSP |
| GGNGEPRGDTYRAY (SEQ ID NO: 20) | BSP |

TABLE 1 -continued

| Sequence | Source |
|---|---|
| CGGNGEPRGDTRAY (SEQ ID NO: 21) | BSP-Y |
| GGNGEPRGDTRAY (SEQ ID NO: 22) | BSP-Y |
| KYGRKRLQVQLSIRT (SEQ ID NO: 23) | mLMα1 res 2719-2730 |
| YGRKRLQVQLSIRT (SEQ ID NO: 24) | mLMα1 res 2719-2730 |
| KGGRNIAEIIKDI (SEQ ID NO: 25) | LMβ1 |
| GGRNIAEIIKDI (SEQ ID NO: 26) | LMβ1 |
| KGGPQVTRGDVFTMP (SEQ ID NO: 27) | VN |
| GGPQVTRGDVFTMP (SEQ ID NO: 28) | VN |
| GRGDSPK (SEQ ID NO: 29) | Short FN |
| KGGAVTGRGDSPASS (SEQ ID NO: 30) | Long FN |
| GGAVTGRGDSPASS (SEQ ID NO: 31) | Long FN |
| Yaa$_1$PQVTRGNVFTMP (SEQ ID NO: 32) | VN |
| RGDYK (SEQ ID NO: 33) | RGD |

It will be understood that the amount of peptide present or accessible from the cell culture surface can vary depending on the composition of the pre-polymers, the length of spacers, and the nature of the polypeptide itself. In addition, different cells in culture may respond differently to the composition of the pre-polymers as well as the identity and amount of peptide available on the surface. It will be understood that certain densities of peptide may be better able to support attachment and proliferation of certain cell types such as, for example, undifferentiated stem cells in a chemically defined medium, although other cell types may proliferate more successfully at different peptide densities.

The polypeptide may be cyclized or include a cyclic portion. Any suitable method for forming cyclic polypeptide may be employed. For example, an amide linkage may be created by cyclizing the free amino functionality on an appropriate amino-acid side chain and a free carboxyl group of an appropriate amino acid side chain. Also, a di-sulfide linkage may be created between free sulfydryl groups of side chains appropriate amino acids in the peptide sequence. Any suitable technique may be employed to form cyclic polypeptides (or portions thereof). By way of example, methods described in, e.g., WO1989005150 may be employed to form cyclic polypeptides. Head-to-tail cyclic polypeptides, where the polypeptides have an amide bond between the carboxy terminus and the amino terminus may be employed. An alternative to the disulfide bond would be a diselenide bond using two selenocysteines or mixed selenide/sulfide bond, e.g., as described in Koide et al, 1993, Chem. Pharm. Bull. 41(3):502-6; Koide et al., 1993, Chem. Pharm. Bull. 41(9):1596-1600; or Besse and Moroder, 1997, Journal of Peptide Science, vol. 3, 442-453.

Polypeptides may be synthesized as known in the art (or alternatively produced through molecular biological techniques) or obtained from a commercial vendor, such as American Peptide Company, CEM Corporation, or GenScript Corporation. Linkers may be synthesized as known in the art or obtained from a commercial vendor, such as discrete polyethylene glycol (dPEG) linkers available from Quanta BioDesign, Ltd.

For any of the polypeptides discussed herein, it will be understood that a conservative amino acid may be substituted for a specifically identified or known amino acid. A "conservative amino acid", as used herein, refers to an amino acid that is functionally similar to a second amino acid. Such amino acids may be substituted for each other in a polypeptide with a minimal disturbance to the structure or function of the polypeptide according to well-known techniques. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q).

Figure 5:
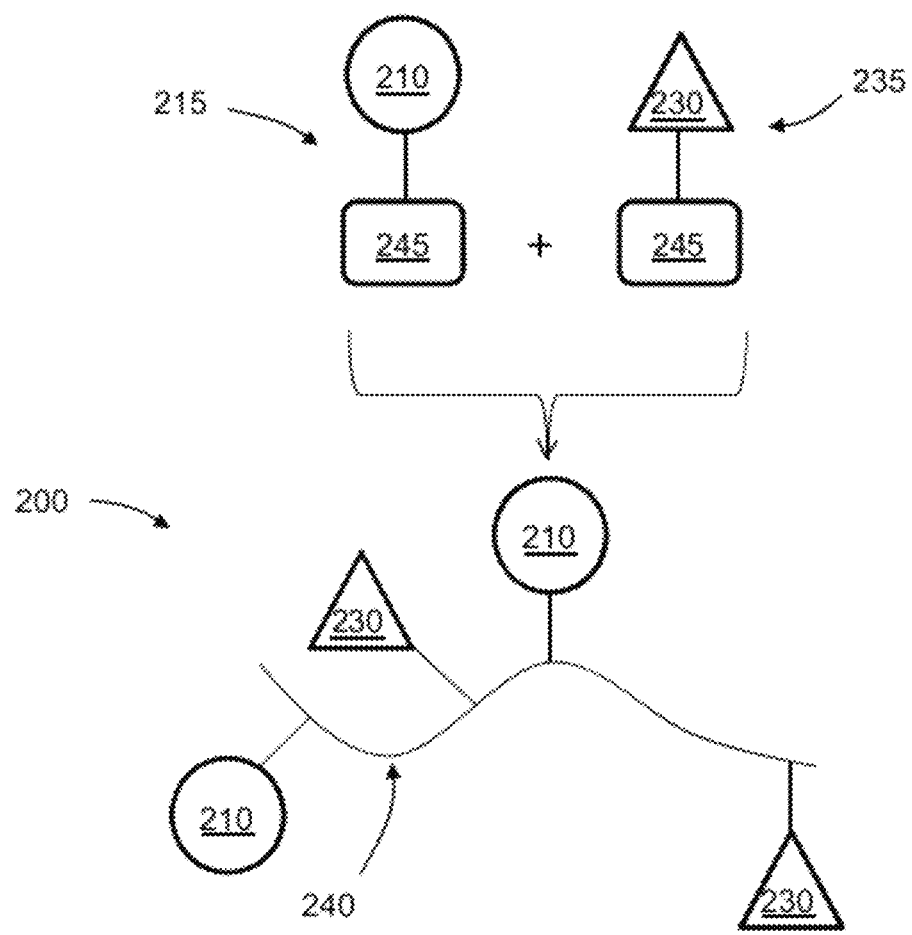
FIG. 5 is a schematic drawing showing a reaction scheme for producing a generic embodiment of a component 2 polymer in accordance with embodiments presented herein.

Whether the component 2 polymer 200 is formed by incorporating a polypeptide 210 into the polymer as it is being formed (e.g., via use of a peptide monomer 215 as shown in FIG. 5) or is conjugated to a polymer after it is formed, the one or more monomers for forming the polymer portion of the component 2 polymer 200 may be selected such that an appropriate peptide density is achieved and appropriate polymer characteristics (e.g, modulus, swellability, etc.) are achieved. One of skill in the art will readily be able to select the appropriate monomers and monomer ratios for preparing polymers having desired characteristics.

Once the appropriate monomers in the appropriate amounts are selected, the polymer may be formed via polymerization reaction (e.g., as discussed above with regard to the component 1 pre-polymer).

In embodiments, the component 2 functionalized peptide polymer 200 has a Mn of >10,000 Daltons (typically 20,000-100,000) Daltons and a Mw >30,000 Daltons (typically 50,000 to 300,000).

III. Coating Compositions

The cationic, cross-linker functionalized pre-polymer ("component 1") and the peptide functionalized polymer ("component 2") may be combined in a coating composition in any suitable amount and ratio.

It has been found that the ratio of cell adhesive polypeptide to cationic moiety may be controlled to enable the binding of stem cells to a coating produced from cross-linking of component 1 (containing the cationic moiety) pre-polymer and component 2 (containing the peptide) peptide polymer, while not forming binding that is too tight to readily harvest the cells. It has been previously suggested that surfaces having cationic moieties, such as tertiary amines, are unsuitable for supporting stem cell growth (see, e.g., Langer et al., "Combinatorial development of biomaterials for clonal growth of human pluripotent stem cells," Nature Materials, vol. 9, September 2010; and "Functional Polymer Hydrogel for Embryonic Stem Cell Support," D. Horak, et al., published online Aug. 3, 2005 in Wiley Interscience). Accordingly, it is surprising that stem cell culture is supported by the coatings described herein. Without intending to be bound by theory, it is believed that having an appropriate amount of cell adhesive peptide allows the cells to initially attach to the coating surfaces described herein, where-after the cells can secrete extracellular matrix (ECM) molecules, which exhibit mostly a net negative charge (proteins, GAGs, etc.) and which readily can adsorb to the positively charged surfaces. However, it cannot be ruled out that non-specific direct cell/substrate interactions, e.g. charges interactions, are also involved.

If cell/substrate interactions are mediated by both cell adhesive peptide-cell interactions and ECM-cell interactions, the ability to readily harvest cells from the coatings described herein may be explained as follows (to which theory the inventors do not wish to be bound). By keeping the concentration of cell adhesive polypeptide low, the specific and robust binding of cells to such peptides is kept to a minimum. Further, ECM molecules are typically easily digested by proteolytic enzymes, such as trypsin. Both of these effects can lead to enhanced cell harvesting. If cell adhesion relies too much to synthetic peptides/cell receptor interactions, then the cell harvesting becomes inefficient. However, if an insufficient quantity of synthetic peptide is present, the coatings may not be able to support the culture of stem cells.

The ratio of component 1 to component 2 may be varied to adjust the concentration of cell binding peptide provided by component 2. In various embodiments, the concentration of cell binding peptide in a coating is less than 5 micrograms per square centimeter of cell culture surface provided by the coating, such as about 1.5 micrograms per square centimeter. Such concentrations of polypeptide are substantially smaller than amounts that have been used with other synthetic surfaces, and can result in significant cost reduction associated with the manufacturing of cell culture articles coated in accordance with the teachings presented herein. It will be understood that altering the components that are used to form component 2, e.g. as discussed above, (in addition to altering the ratio of component 1 to component 2) may be used to adjust the amount polypeptide that ultimately results in a coating.

The cationic moiety, such as the tertiary amine moiety, may be present in a coating composition at any suitable concentration. As with the polypeptide concentration, the ratio of component 1 to component 2 may be varied to control the concentration of the cationic moiety. It will be understood that altering the components that are used to form component 1, e.g. as discussed above, (in addition to altering the ratio of component 1 to component 2) may be used to adjust the amount cationic moiety that ultimately results in a coating.

In some embodiments, weight percent of component 1 in the blend or other composition is from 30 to 70%; e.g. from 40 to 60 wt %, and component 2 is present at a weight percent of 70 to 30; e.g. from 40 to 60 wt %. Of course, the relative percentages of component 1 and component 2 pre-polymers may be varied based on the actual composition of the pre-polymers themselves to achieve desired amounts of polypeptide and cationic moiety.

In some embodiments the component 1 and component 2 pre-polymers are dissolved in a solvent for use in a coating process (as described below). Any suitable solvent may be used. In some embodiments, the solvent is trifluoroethanol (TFE).

In some embodiments, a blend of solution containing the appropriate ratio of component 1 and component 2 pre-polymers for coating a cell culture article are packaged in a container, such as a vial or ampule, and provided with a cell culture article so that an end user can coat the article in the end user's laboratory. In some embodiments, more than one container, each containing different ratios of component 1 and component 2 or different component 1 pre-polymer or component 2 peptide polymer are provided so that the end user may select the appropriate combination for use with the cells and culture conditions they intend to employ.

The component 1 pre-polymer and component 2 peptide polymer in solution may be in solution at any suitable concentration. In various embodiments, the combined concentration of the component 1 pre-polymer and component 2 peptide-polymer is 10 mg/ml or less, such as 5 mg/ml or less, or about 1 mg/ml.

IV. Coating Process

Component 1 pre-polymer and component 2 peptide-polymer may be disposed onto a cell culture article in any suitable manner. Generally, a solution containing the component 1 pre-polymer and component 2 peptide polymer, as described above, is disposed on a surface of the cell culture article. The solution may be sprayed onto the surface of the article, may be poured on the surface of the article, or the like. In some embodiments, the article is submerged and removed from the solution.

Figure 7:
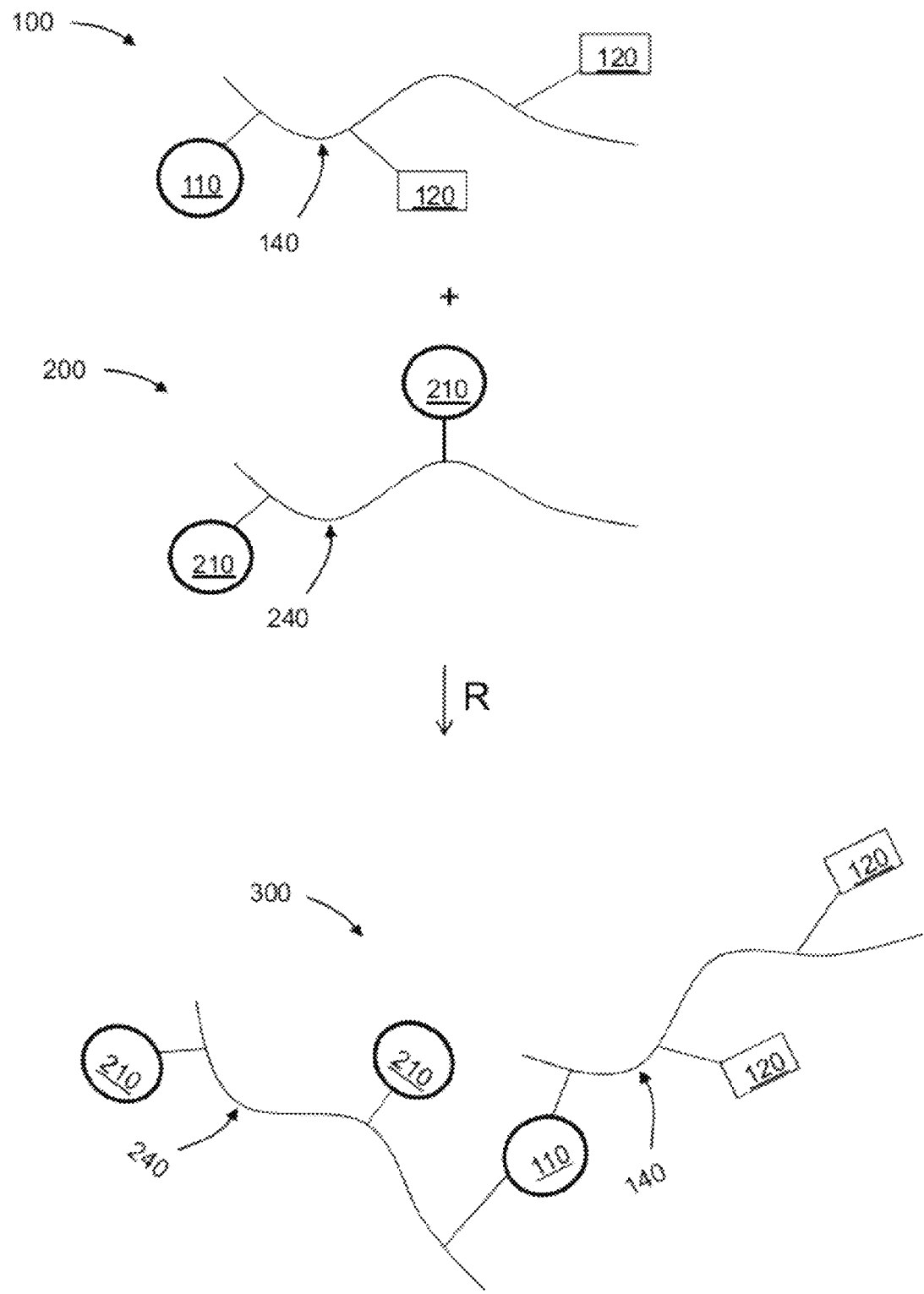
FIG. 7 is a schematic drawing of a reaction scheme for cross-linking a pre-polymer and a peptide polymer in accordance with embodiments presented herein.

Once the solution is disposed on the surface of the article, the coated article is subjected to electromagnetic radiation or other suitable conditions to activate the cross-linker moiety of the component 1 pre-polymer. For example and with reference to FIG. 7, exposing a mixture of component 1 pre-polymer 100 and component 2 peptide-polymer 200 to radiation R (other other suitable conditions) causes activation of the cross-linker moiety 110 of the component 1 pre-polymer 100, which can cross-link with the polymer backbone 240 of the component 2 polymer 200 resulting in a cross-linked polymer 300 having cationic moieties 120 and polypeptide moieties 210, rendering the polymer 300 coating suitable for cell culture, particularly for culture of stem cells. While not shown it will be understood that cross linking between the cross-linker moiety 110 and the backbone 140 of the component 1 pre-polymer 100 may also occur.

Figure 8:
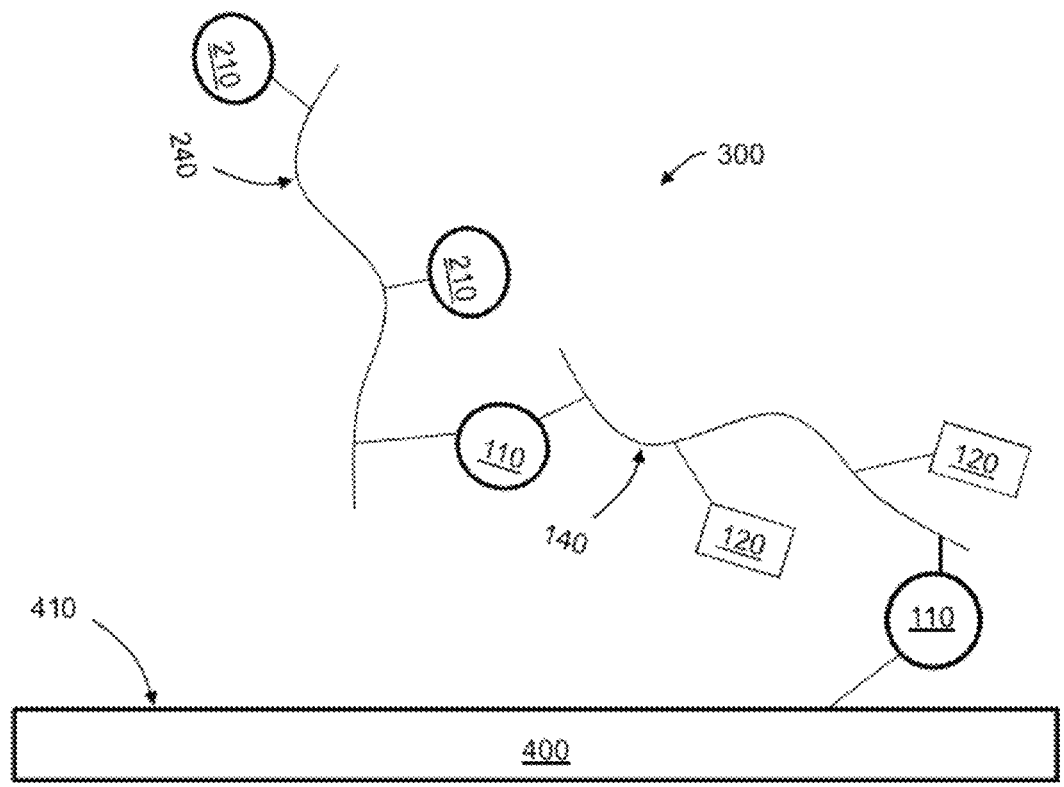
FIG. 8 is a schematic diagram of a coated surface of a cell culture article in accordance with embodiments presented herein.

Referring to FIG. 8, when the mixture of components 1 and 2 100, 200 are exposed to radiation while the mixture is in contact with a surface 410 of a cell culture article 400, a cross-linker moiety 110 of the component 1 pre-polymer may bind to the surface 410 of the article 400, providing a covalently attached surface coating 300 having cationic moieties 120 and polypeptide moieties 210.

Of course, the coating 300 may be attached to the surface 410 of the article 400 via non covalent interactions. Examples of non-covalent interactions that may attach the polymer 300 with the substrate include chemical adsorption, hydrogen bonding, surface interpenetration, ionic bonding, van der Waals forces, hydrophobic interactions, dipole-dipole interactions, mechanical interlocking, and combinations thereof.

Regardless of how the polymer coating 300 attaches to the surface 410 of the article 400, the polymer 300 preferably attaches such that it does not delaminate during cell culture conditions, such as in the presence of cell culture media at 37° C.

Figure 9:
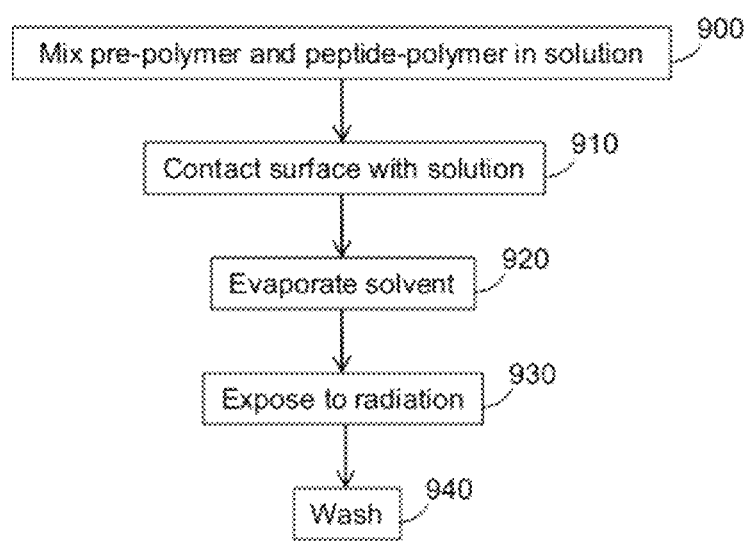
FIG. 9 is a flow diagram depicting a method for coating a cell culture article in accordance with embodiments presented herein.

Referring now to FIG. 9, an overview of a method for coating a cell culture article is presented. The method includes mixing component 1 pre-polymer and component 2 peptide-polymer in a solution (900), contacting the surface of the cell culture article with the solution (910), evaporating the solvent (920), exposing the mixture contacted with the surface of the article to radiation to activate the cross-linker moieties of the component 1 pre-polymer (930) and washing to remove unbound materials (940).

The solvent may be removed by passive drying. Alternatively, heat or vacuum may be applied to facilitate evaporation.

Any suitable amount or type of electromagnetic radiation may be used to activate the cross-linker moiety of the component 1 pre-polymer. For example, when a benzophenone cross-linker moiety is employed, the coated cell culture article may be exposed to UV light. It has been found that coated articles illuminated with UV light under ambient atmosphere show good attachment. By way of example, a fusion lamp equipped with a "D" bulb at a 80% power with a 0.6 m/min belt speed has been found to be sufficient in some embodiments. To avoid degradation of the polypeptide by highly energetic low wavelength radiation, a filter screening wavelengths below 300 nm may be placed between the light source and the coating composition. In the case of a polystyrene well plate, its lid or bottom plate can be advantageously used as an effective filter blocking the potentially deleterious low wavelength radiation.

The surface of the cell culture article to which the polymer is coated may be formed of any suitable material. For example, the surface of the cell culture article may be formed from a ceramic substance, a glass, a plastic, a polymer or co-polymer, any combinations thereof, or a coating of one material on another. Such base materials include glass materials such as soda-lime glass, pyrex glass, vycor glass, quartz glass; silicon; plastics or polymers, including dendritic polymers, such as poly(vinyl chloride), poly(vinyl alcohol), poly(methyl methacrylate), poly(vinyl acetate-co-maleic anhydride), poly(dimethylsiloxane) monomethacrylate, cyclic olefin polymers, fluorocarbon polymers, polystyrenes, polypropylene, polyethyleneimine; copolymers such as poly(vinyl acetate-co-maleic anhydride), poly(styrene-co-maleic anhydride), poly(ethylene-co-acrylic acid) or derivatives of these or the like.

It has been found that good attachment results when the substrate is corona treated or plasma treated. Examples of vacuum or atmospheric pressure plasma include RF and microwave plasmas both primary and secondary, dielectric barrier discharge, and corona discharge generated in molecular or mixed gases including air, oxygen, nitrogen, argon, carbon dioxide, nitrous oxide, or water vapor. By way of example, plasma treated polystyrene, such as TCT polystyrene or CellBIND® treated polystyrene (Corning, Inc.) provide good substrates for attachment.

VI. Cell Culture Article

A coating as described herein may be attached to the surface of any suitable cell culture article, such as single and multi-well plates, such as 6, 12, 96, 384, and 1536 well plates, jars, petri dishes, flasks, beakers, plates, roller bottles, slides, such as chambered and multichambered culture slides, tubes, cover slips, bags, membranes, hollow fibers, beads and microcarriers, cups, spinner bottles, perfusion chambers, bioreactors, CellSTACK® (Corining, Inc.) and fermenters.

VII. Incubating Cells on Synthetic Polymer Coatings

A cell culture article having a coating as described above may be seeded with cells. The cells may be of any cell type. For example, the cells may be connective tissue cells such as epithelial and endothelial cells, hepatocytes, skeletal or smooth muscle cells, heart muscle cells, intestinal cells, kidney cells, or cells from other organs, stem cells, islet cells, blood vessel cells, lymphocytes, cancer cells, or the like. The cells may be mammalian cells, preferably human cells, but may also be non-mammalian cells such as bacterial, yeast, or plant cells.

In numerous embodiments, the cells are stem cells which, as generally understood in the art, refer to cells that have the ability to continuously divide (self-renewal) and that are capable of differentiating into a diverse range of specialized cells. In some embodiments, the stem cells are multipotent, totipotent, or pluripotent stem cells that are isolated from an organ or tissue of a subject. Such cells are capable of giving rise to a fully differentiated or mature cell types. A stem cell may be a bone marrow-derived stem cell, autologous or otherwise, a neuronal stem cell, or an embryonic stem cell. A stem cell may be nestin positive. A stem cell may be a hematopoeietic stem cell. A stem cell may be a hematopoeietic stem cell. A stem cell may be a multi-lineage cell derived from epithelial and adipose tissues, umbilical cord blood, liver, brain or other organ. In various embodiments, the stem cells are undifferentiated stem cells, such as undifferentiated embryonic stem cells.

Prior to seeding cells, the cells may be harvested and suspended in a suitable medium, such as a growth medium in which the cells are to be cultured once seeded onto the surface. For example, the cells may be suspended in and cultured in a serum-containing medium, a conditioned medium, or a chemically-defined medium. As used herein, "chemically-defined medium" means cell culture media that contains no components of unknown composition. Chemically defined media may, in various embodiments, contain no proteins, hydrosylates, or peptides of unknown composition. In some embodiments, conditioned media contains polypeptides or proteins of known composition, such as recombinant growth hormones. Because all components of chemically-defined media have a known chemical structure, variability in culture conditions and thus cell response can be reduced, increasing reproducibility. In addition, the possibility of contamination is reduced. Further, the ability to scale up is made easier due, at least in part, to the factors discussed above. Chemically defined cell culture media are commercially available from Invitrogen (Invitrogen Corporation, 1600 Faraday Avenue, PO Box 6482, Carlsbad, Calif. 92008) as STEM PRO, a fully serum- and feeder-free (SFM) specially formulated from the growth and expansion of embryonic stem cells, and Stem Cell Technologies, Inc. as mTeSR™1 maintenance media for human embryonic stem cells. Another chemically-defined medium is MesenCult®-XF Medium which is a standardized, xeno-free, serum-free medium for the culture of human mesenchymal stem cells (MSCs). MesenCult®-XF Medium is available from STEMCELL Technologies Inc.

One or more growth or other factors may be added to the medium in which cells are incubated with the synthetic hydrogel layer. The factors may facilitate cellular proliferation, adhesion, self-renewal, differentiation, or the like. Examples of factors that may be added to or included in the medium include muscle morphogenic factor (MMP), vascular endothelium growth factor (VEGF), interleukins, nerve growth factor (NGF), erythropoietin, platelet derived growth factor (PDGF), epidermal growth factor (EGF), activin A (ACT), hematopoietic growth factors, retinoic acid (RA), interferons, fibroblastic growth factors, such as basic fibroblast growth factor (bFGF), bone morphogenetic protein (BMP), peptide growth factors, heparin binding growth factor (HBGF), hepatocyte growth factor, tumor necrosis factors, insulin-like growth factors (IGF) I and II, transforming growth factors, such as transforming growth factor-$\beta$1 (TGF$\beta$1), and colony stimulating factors.

The cells may be seeded at any suitable concentration. Typically, the cells are seeded at about 10,000 cells/cm$^2$ of substrate to about 500,000 cells/cm$^2$. For example, cells may be seeded at about 50,000 cells/cm² of substrate to about 150,000 cells/cm². However, higher and lower concentrations may readily be used. The incubation time and conditions, such as temperature, $CO_2$ and $O_2$ levels, growth medium, and the like, will depend on the nature of the cells being cultured and can be readily modified. The amount of time that the cells are incubated on the surface may vary depending on the cell response desired.

The cultured cells may be used for any suitable purpose, including (i) obtaining sufficient amounts of undifferentiated stem cells cultured on a synthetic surface in a chemically defined medium for use in investigational studies or for developing therapeutic uses, (ii) for investigational studies of the cells in culture, (iii) for developing therapeutic uses, and (iv) for therapeutic purposes.

OVERVIEW OF ASPECTS OF DISCLOSURE

In a first aspect, a composition for forming a polymeric cell culture surface includes (i) a pre-polymer comprising a polymer backbone, a cationic moiety conjugated to the backbone, and a cross-linker moiety conjugated to the backbone; and (ii) a peptide-polymer comprising a polymer backbone and cell adhesive peptide conjugated to the backbone.

A second aspect is a composition of the first aspect, wherein the cationic moiety is an amine moiety.

A third aspect is a composition of the first aspect, wherein the amine moiety is a tertiary amine.

A fourth aspect is a composition of the third aspect, wherein the tertiary amine is selected from the group consisting of an alkylamine or an alkanolamine.

A fifth aspect is a composition of the first aspect, wherein the cationic moiety conjugated to the polymer backbone results from polymerization of a monoalkylaminoalkyl or dialkylaminoalkyl (meth)acrylate monomer into the pre-polymer.

A sixth aspect is a composition of the first aspect, wherein the cationic moiety conjugated to the polymer backbone results from the polymerization of a monomer into the first pre-polymer, wherein the monomer is selected from the group consisting of an N,N-dimethylaminoethyl(meth)acrylate, an N,N-diethylaminoethyl (meth)acrylate, an N,N-dipropylaminoethyl (meth)acrylate and an N-tert-butylaminoethyl (meth)acrylate.

A seventh aspect is a composition of the first aspect, wherein the cationic moiety conjugated to the polymer backbone results from polymerization of a 2-(dimethylamino)ethyl methacrylate (DMEMA) monomer into the pre-polymer.

An eighth aspect is a composition of any of the first seven aspects, wherein the pre-polymer further comprises a hydrophilic moiety conjugated to the polymer backbone of the pre-polymer.

A ninth aspect is a composition of the eighth aspect, wherein the hydrophilic moiety conjugated to the polymer backbone results from polymerization of a monomer into the pre-polymer, wherein the monomer is selected from the group consisting of 2-carboxyethyl methacrylate, 2-carboxyethyl acrylate, acrylic acid, methacrylic acid, hydroxypropyl methacrylate, 2-hydroxyethyl methacrylate (HEMA), 2-hydroxyethyl acrylate, glycerol methacrylate, hydroxypropyl acrylate, 4-hydroxybutyl acrylate, 2-carboxyethyl acrylate, acrylamidoglycolic acid, N-(hydroxymethyl)acrylamide, N-[Tris(hydroxymethyl)methyl] acrylamide, 3-acryloylamino-1-propanol, N-acrylamidoethoxyethanol, and N-hydroxyethyl acrylamide.

A tenth aspect is a composition of the eighth aspect, wherein the hydrophilic moiety conjugated to the polymer backbone results from polymerization of a 2-hydroxyethyl methacrylate (HEMA) monomer into the pre-polymer.

An eleventh aspect is a composition of any of the first ten aspects, wherein the cross-linker moiety is a benzophenone moiety.

A twelfth aspect is a composition according to any of the first eleven aspects, wherein the cell adhesive peptide comprises an R-G-D sequence.

A thirteenth aspect is a composition according to any of the first eleven aspects, wherein the cell adhesive peptide is a sequence of amino acids found in vitronectin, laminin, bone sialoprotein, collagen, or fibronectin.

A fourteenth aspect is a composition of any of the first eleven aspects, wherein the cell adhesive peptide comprises a sequence of amino acids selected from the group consisting of: KGGGQKCIVQTTSWSQCSKS (SEQ ID NO:1), GGGQKCIVQTTSWSQCSKS (SEQ ID NO:2), KYGLALERKDHSG (SEQ ID NO:3), YGLALERKDHSG (SEQ ID NO:4), KGGSNNNRHSIYITRFGNMGS (SEQ ID NO:5), GSINNNRHSIYITRFGNMGS (SEQ ID NO:6), KGGTWYKIAFQRNRK (SEQ ID NO:7), GGTWYKIAFQRNRK (SEQ ID NO:8), KGGTSIKIRGTYSER (SEQ ID NO:9), GGTSIKIRGTYSER (SEQ ID NO:10), KYGTDIRVTLNRLNTF (SEQ ID NO:11), YGTDIRVTLNRLNTF (SEQ ID NO:12), KYGSETTVKYIFRLHE (SEQ ID NO:13), YGSETTVKYIFRLHE (SEQ ID NO:14), KYGKAFDITYVRLKF (SEQ ID NO:15), YGKAFDITYVRLKF (SEQ ID NO:16), KYGAASIKVAVSADR (SEQ ID NO:17), YGAASIKVAVSADR (SEQ ID NO:18), CGGNGEPRGDTYRAY (SEQ ID NO:19), GGNGEPRGDTYRAY (SEQ ID NO:20), CGGNGEPRGDTRAY (SEQ ID NO:21), GGNGEPRGDTRAY (SEQ ID NO:22), KYGRKRLQVQLSIRT (SEQ ID NO:23), YGRKRLQVQLSIRT (SEQ ID NO:24), KGGRNIAEIIKDI (SEQ ID NO:25), GGRNIAEIIKDI (SEQ ID NO:26), KGGPQVTRGDVFTMP (SEQ ID NO:27), GGPQVTRGDVFTMP (SEQ ID NO:28), GRGDSPK (SEQ ID NO:29), KGGAVTGRGDSPASS (SEQ ID NO:30), GGAVTGRGDSPASS (SEQ ID NO:31), $Yaa_1$PQVTRGNVFTMP (SEQ ID NO:32), RGDYK (SEQ ID NO:33), and combinations thereof.

A fifteenth aspect is a composition according to any of the first fourteen aspects, wherein the cell adhesive polypeptide is incorporated into the peptide-polymer from a peptide monomer of the formula $R_m$—$S_p$—$C_{ap}$; wherein R is a polymerization moiety selected from the group consisting of acrylate, methacrylate, acrylamide, methyacrylamide, maleimide and fumarate and any combination thereof, and m is an integer greater than 1; wherein $S_p$ is an optional spacer moiety wherein the spacer moiety comprises polyethylene oxide or polypropylene oxide having the formula (O—$CH_2CHR'$)$_{m2}$ where R' is H or $CH_3$ and m2 is an integer from 0 to 20, or $Xaa_n$ wherein Xaa is independently any amino acid and n is an integer from 0 to 20, or any combination thereof; and, wherein $C_{ap}$ is a peptide comprising a cell adhesive sequence.

A sixteenth aspect is a composition of any of the first fifteen aspects, wherein the peptide-polymer further comprises a hydrophilic moiety conjugated to the backbone of the peptide-polymer.

A seventeenth aspect is a composition of the sixteenth aspect, wherein the hydrophilic moiety conjugated to the polymer backbone results from polymerization of a monomer into the second pre-polymer, wherein the monomer is selected from the group consisting of 2-carboxyethyl methacrylate, 2-carboxyethyl acrylate, acrylic acid, methacrylic acid, hydroxypropyl methacrylate, 2-hydroxyethyl methacrylate (HEMA), 2-hydroxyethyl acrylate, glycerol methacrylate, hydroxypropyl acrylate, 4-hydroxybutyl acrylate, 2-carboxyethyl acrylamide, acrylamidoglycolic acid, N-(hydroxymethyl)acrylamide, N-[Tris(hydroxymethyl)methyl]acrylamide, 3-acryloylamino-1-propanol, N-acrylamidoethoxyethanol, and N-hydroxyethyl acrylamide.

An eighteenth aspect is a composition of the sixteenth aspect, wherein the hydrophilic moiety conjugated to the polymer backbone results from polymerization of a 2-hydroxyethyl methacrylate (HEMA) monomer into the peptide-polymer.

A nineteenth aspect is a composition of any of the first eighteen aspects, wherein the peptide-polymer comprises the polymerization product of an ethylenically unsaturated monomer having a carboxyl group with an ethylenically unsaturated monomer not having a carboxyl group, wherein the cell adhesive peptide is conjugated to the pre-polymer via the carboxyl group.

A twentieth aspect is a composition of the nineteenth aspect, wherein the ethylenically unsaturated monomer not having the carboxyl group is hydrophilic.

A twenty-first aspect is a method of making a cell culture article comprising providing the pre-polymer and peptide-polymer of any one of the first twenty aspects to a substrate and exposing the pre-polymer and peptide-polymer on the substrate to an energy source to cross-link the pre-polymer and peptide-polymer to each other and to the substrate.

A twenty-second aspect is a cell culture article made by the method of the twenty-first aspect.

A twenty-third aspect is the cell culture article of the twenty-second aspect, wherein the concentration of the polypeptide is less than 5 micrograms per square centimeter of a surface of the substrate.

In the following, non-limiting examples are presented, which describe various embodiments of the articles and methods discussed above.

EXAMPLES

Example 1: Preparation of Component (i): Photo-Reactive Hydrogel Forming Copolymer (Photo-DMAE)

Step a: Synthesis of 4-benzoylbenzoyl chloride

Briefly, five grams of 4 benzoyl benzoic acid was placed in a 100 ml round bottom flask to which thionyl chloride (15 ml) was added. The resulting suspension was heated to reflux for one hour, during which time all solids were dissolved. Volatile compounds were removed by rotary evaporation. The residue was dissolved in toluene and again evaporated. This was done two times in order to remove all thionyl chloride. The crude compound can be purified further by re-crystallization from petroleum ether (Attention the solubility is about 1 g per 100 ml). The product is a white powder, Mp. 95° C. (Lit: 98-99° C.). The $^1$H-NMR corresponds to the literature data. $^1$H NMR (400 MHz, CDCl3) δ 8.20 (d, J=7.5, 2H), 7.86 (d, J=7.4, 2H), 7.78 (d, J=7.4, 2H), 7.61 (d, J=6.7, 1H), 7.49 (t, J=7.4, 2H) ppm. $^{13}$C NMR (101 MHz, CDCl3) δ 195.31, 167.85, 143.27, 136.36, 135.75, 133.34, 131.15, 130.09, 130.01, 128.59 ppm. Note: Hydrolysis can be easily seen in the carbon spectra the =O signal is at 170.42 ppm.

Step b: Synthesis of N-(3-methacrylamidopropyl)-4-benzoylbenzamide 730 mg (4.1 mmol) of N(3-aminopropyl)methacrylamide hydrochloride was solved in 25 ml dichloromethane in a 50 ml round bottom flask. One gram (4.1 mmol) of 4-benzoylbenzoyl chloride and phenothiazine (1 mg; as polymerization inhibitor) were added as a solid. The suspension was cooled with an ice bath while triethyl amine (1.3 ml, 10 mmol) was added. The ice bath was removed and stirred for 3 h. The organic phase was washed twice with 0.1 N HCl and dried over sodium sulfate. The solvent was evaporated under reduced pressure. The remaining crude product was purified by Flash column chromatography using ethyl acetate as solvent (Rf=0.5). The yield was 510 mg (36%) of the pure compound. $^1$H NMR (400 MHz, CDCl$_3$) δ 8.01 (d, J=7.5, 2H), 7.86 (d, J=7.4, 2H), 7.80 (d, J=7.2, 2H), 7.62 (s, 1H), 7.51 (d, J=7.5, 2H), 5.81 (s, 1H), 5.39 (s, 1H), 3.49 (4H), 2.01 (s, 3H), 1.79 (s, 2H). $^{13}$C NMR (101 MHz, CDCl3) δ 196.05, 169.53, 166.74, 139.93, 139.52, 137.63, 137.07, 132.79, 130.13, 130.06, 128.39, 127.00, 120.29, 35.98, 29.76, 18.68.

Step c: Synthesis of Photo-Reactive Hydrogel Forming Copolymer (Photo-DMAE)

Figure 10:
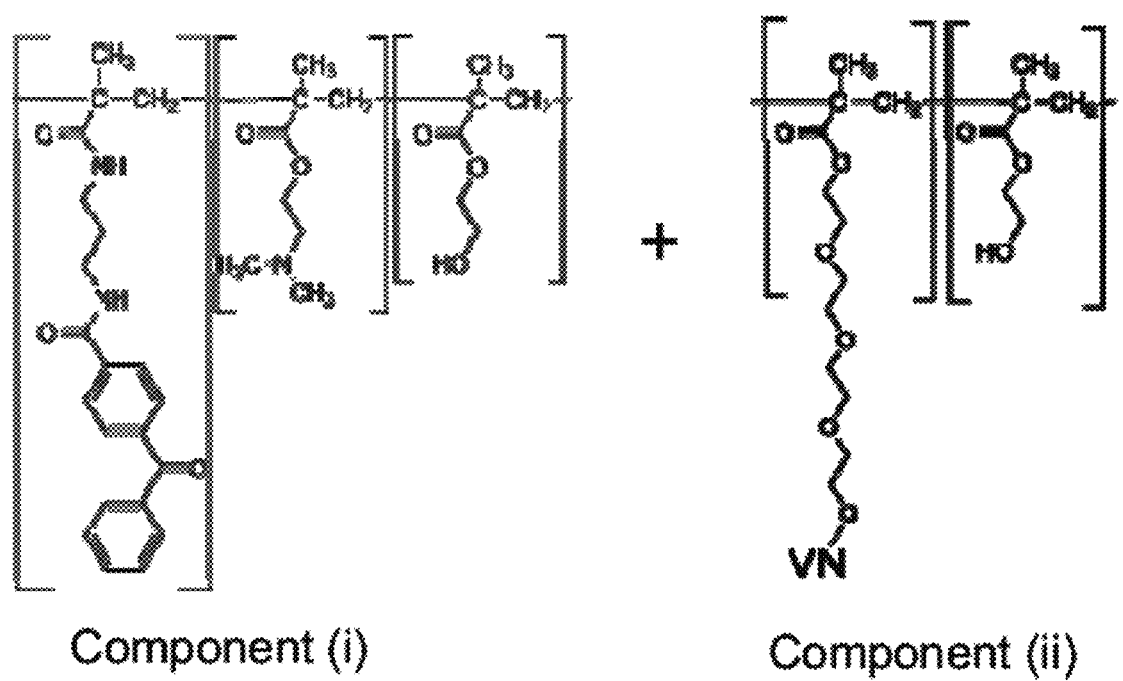
FIG. 10 is a reaction scheme showing example of formula of components (i) and (ii) to be blended together to prepare a coating composition.

Photo-DMAE was prepared accordingly to the reaction given in FIG. 10. Briefly, 2-(dimethylamino) ethyl methacrylate (DMEMA), 0.42 g (2.67 mmol), and 2-Hydroxyethylmethacrylate HEMA, 0.983 g (7.55 mmol), were added to 20 ml dimethyl sulfoxide (DMSO) weighted in a amber flask equipped with a stir bar, to which N-(3-methacrylamidopropyl)-4-benzoylbenzamide, 0.17 g (0.48 mmol) was added and dissolved in this solution. After dissolution, 2,2'-Azobis-(2-Methylbutyronitrile), 40 mg (0.21 mmol), was added and stirred until the dissolution was complete. The solution was deoxygenated by means of argon bubbling for 1 minute. The sealed flask was then heated for 20 hours at 68° C. under mixing and protected from light. After cooling to room temperature, the polymer was isolated by precipitation in 250 ml DI water. The sticky polymer collected was dissolved in ethanol and precipitate in diisopropylether. The solid obtained was washed three times with diisopropyl ether and then was vacuum dried to yield a fine white product.

The molecular weight of the PhotoDMAE polymer was determined by size exclusion chromatography (SEC) coupled with a refractive Index detector, a light scattering detector, a photodiode array detector and a viscometer detector. The mobile phase was trifluoroethanol+potassium trifluoroacetate. Average Mw was 90.950 and Mn was 35.090 and PDI was 2.59.

Example 2: Synthesis of Component (ii): poly (HEMA-co-MAA-PEG4-VN)

Step A: Synthesis of (MAA-PEG4-VN)

The VN peptide (KGGPQVTRGDVFTMP SEQ ID NO:27) was synthesized and provided by American Peptide, Sunnyvale, Calif. by the following process.

MAA-PEO4-Lys-Gly-Gly-Pro-Gln-Val-Thr-Arg-Gly-Asp-Val-Phe-Thr-Met-Pro-NH2 (SEQ ID NO:27): The peptide was synthesized on 1 mmol Fmoc-Rink Amide resin via Fmoc chemistry. Protecting groups used for amino acids were: t-Butyl group for and Asp and Thr, Trt group for Gln, Pbf for Arg, Boc for Lys. Fmoc protected amino acids were purchased from EMD Biosciences; Fmoc-PEG4-OH was purchased from Quanta Biodesign. Reagents for coupling and cleavage were purchased from Aldrich. Solvents were purchased from Fisher Scientific. The peptide chain was assembled on resin by repetitive removal of the Fmoc protecting group and coupling of protected amino acid. HBTU and HOBt were used as coupling reagents and NMM was used as base. 20% piperidine in DMF was used as de-Fmoc-reagent. Methacrylic acid (MAA) was coupled to the amino group of PEG4 after removal of the Fmoc protecting group. After the last coupling, resin was treated with TFA/TIS/H2O (95:3:2, v/v/v) for cleavage and removal of the side chain protecting groups. Crude peptide was precipitated from cold ether and collected by filtration. Crude peptide was purified by reverse-phase HPLC; collected fractions with purity over 90% were pooled and lyophilized. The products were provided by American Peptide in ≥90% purity and were used without further purification. Ethanol was used as non-reactive diluents in the process and was purchased from Sigma-Aldrich.

Step B: Preparation of poly
(HEMA-co-MAA-PEO4-VN)

HEMA, 60 mg (0.46 mmol), and Vitronectine-PEG4-Methacrylate (MAA-PEO4-VN), 100 mg (0.05 mmol), were added to 7.5 ml ethanol in an amber flask equipped with a stir bar. Then 2,2'-Azobis-(2-Methylbutyronitrile), 9 mg, was added and stirred until completed dissolution. The solution was deoxygenated with an argon purge for 1 minute. The sealed flask was then heated for 24 hours at 68° C. under mixing and protected from light. After cooling to RT, the poly (HEMA-co-MAA-PEO4-VN) polymer was isolated by pouring the crude reaction medium in ethylacetate. The white solid obtained was washed 3 times with diisopropyl ether and vacuum dried. Although the coatings described below have been made without any purification of the poly (HEMA-co-MAA-PEO4-VN) polymer, unreacted peptides can be easily removed by means of well known processes such as continuous or discontinuous diafiltration process. Particularly efficient unreacted peptide removal can be performed using for example a 5,000 MWCO Corning Spin-X concentrator column.

The polymer can be stored at 4° C. for several months.

Molecular weight was determined by size exclusion chromatography (SEC) coupled with a refractive Index detector, a light scattering detector, a photodiode array detector and a viscometer detector. The mobile phase was trifluoroethanol+potassium trifluoroacetate. Average Mw was 80,000 to 100,000 and Mn was 25.000 to 33.000 and PDI was 2.8.

Example 3: Coating of 6-Well Plates

A coating formulation was prepared by blending 40 wt % Photo-DMAE as component (i) and 60 wt % poly (HEMA-co-VNPEGMAA) as component (ii) at 1 mg/ml total solid contents in trifluoroethanol (TFE) available from Sigma Aldrich.

Tissue Culture Treated (TCT) polystyrene (PS) 6-well plates (Corning Incorporated) were used. 40 µl/well were dispensed (by hand using ¼-inch hole-template lid). The lid was replaced immediately hole-template lid by cover-plate. The formulation was allowed to spread to the edge with cover-plate in place for 5 to 8 min Plates were allowed to dry by replacing the cover plate with filter paper 15 min at 40° C. (or vacuum drying) UV curing was done with a "D" bulb, 80% power, 0.6 m/min belt speed, 1 pass, plate are exposed upside-down with the lid in place to avoid contamination by dusts (the bottom plate plays the role of UV filter protecting peptide owing to the its intrinsic adsorption of wavelengths <300 nm). Plates were washed with 1% wt/v SDS for 1 hour then four times rinsed with DI water and finally dried under gentle nitrogen flow. Optionally, the plates were washed with ethanol or ethanol 70% v/v in water (to ensure sanitization).

Figure 11:
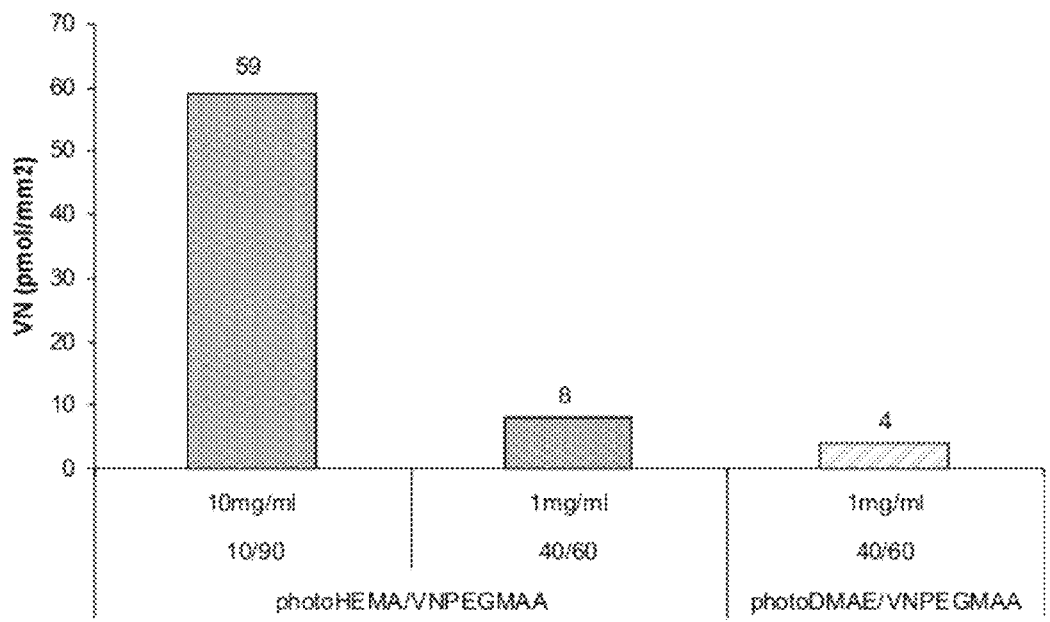
FIG. 11 is a bar graph showing amount of immobilized peptide (pmol/mm$^2$) quantified by BCA, for plates prepared in accordance with Examples 3, 6 and 7.

The amount of immobilized peptide was quantified by BCA. The results are shown in FIG. 11.

Example 4: Coating CellSTACK™ Vessels 40 ml coating composition was prepared by blending 40 wt % Photo-DMAE as component (i) and 60 wt % poly (HEMA-co-VNPEGMAA) as component (ii) at 1 mg/ml total solid contents in TFE.

10 ml of the solution was dispensed in a CellBIND® CellSTACK® one layer vessel. After spreading, the excessive liquid (about 7 ml) was carefully aspirated and the vessel was dried upside down at 40° C. for 15 min.

After cooling, the vessel was exposed to about 9.000 mJ/cm$^2$ UV-A using a 12 "Fusion lamp equipped with D bulbs (width achieved by stacking end-to-end two 6 "lamps). After cooling, the vessel was washed with 50 ml 1% wt/v aqueous SDS solution for 1 hour, then washed 4 times with DI water and finally dried.

Figure 17:
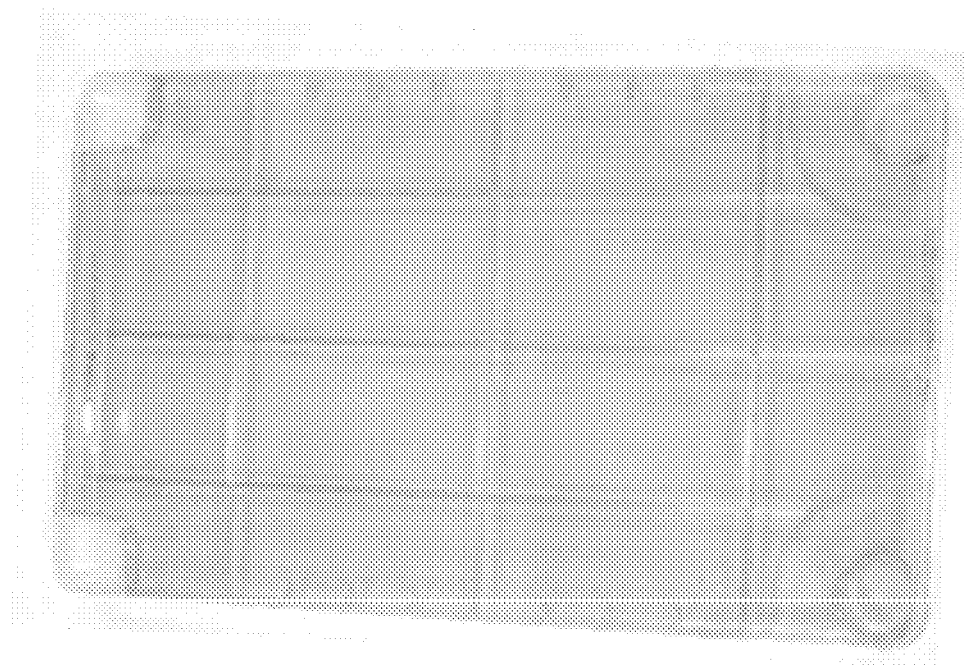
FIG. 17 is a photograph showing colloidal gold staining of a CellSTACK™ vessel coated in accordance with the teachings presented herein.

FIG. 17 is an image of a colloidal gold-stained (Colloidal Gold Total Protein Stain reagent available from Bio-Rad, Hercules, Calif.) CellSTACK™ vessel, indicating that large sized vessels can be uniformly coated with the coatings described herein.

Figure 12:
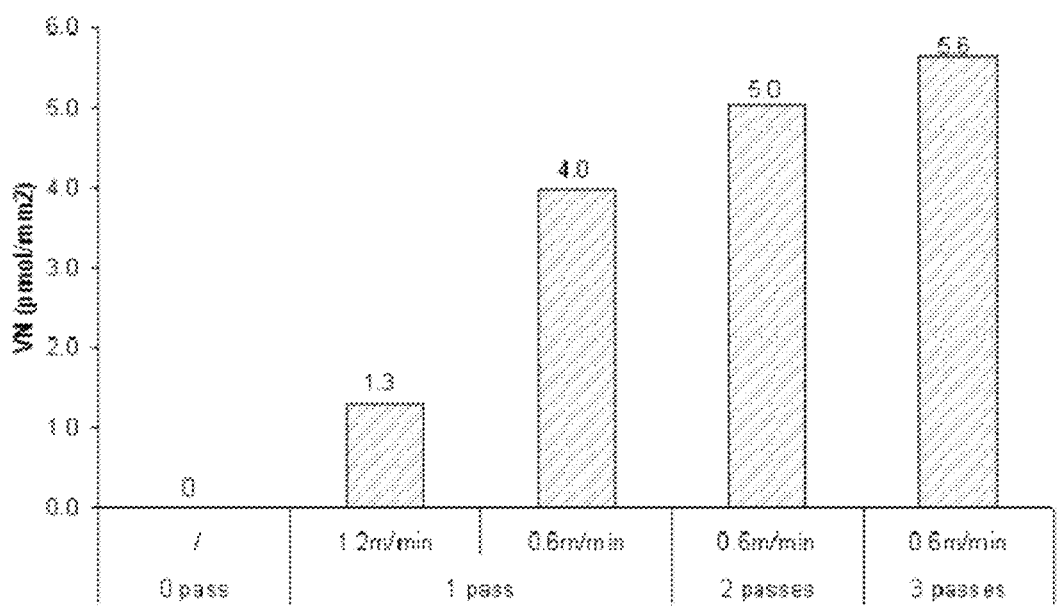
FIG. 12 is a bar graph showing amount of immobilized peptide (pmol/mm$^2$) quantified by BCA for plates prepared in accordance with Example 5.

Example 5: Coating of 6-Well Plates with Different Levels of UV Curing 6-well plates were prepared as described in EXAMPLE 3 except that UV curing was done with 0, 1, 2 or 3 passes at 0.6 m/min belt speed, or 1 pass at 1.2 m/min belt. Following washing, immobilized peptide was quantified by BCA. The results are presented in FIG. 12, which shows a clear UV dose-response.

Example 6: Comparative Example 1 (PCT Patent Application No. PCT/FR10/000,553, filed on Jul. 28, 2010 (SP10-205))

A coating formulation was prepared by blending 10 wt % Photo-HEMA as component and 90 wt % poly (HEMA-co-VNPEGMAA) as component at 10 mg/ml total solid contents in trifluoroethanol, as described in PCT Patent Application No. PCT/FR10/000,553 filed Jul. 28, 2010. 6-well plates were prepared with this solution as described in EXAMPLE 3 above.

The amount of immobilized peptide was quantified by BCA. The results are shown in FIG. 11.

These substrates adequately supported the culture of embryonic stem cells (see FIG. 13c and associated discussion below in EXAMPLE 9 below) and mesenchymal stem cells, but cell harvesting was less efficient than achieved with MesenCult® attachment substrate (see FIG. 16) and associated discussion in EXAMPLE 8 below) and peptide consumption is high owing to the 10 mg/ml solution (see FIG. 11).

Example 7: Comparative Example 2

A coating formulation was prepared by blending 40 wt % Photo-HEMA as component and 60 wt % poly (HEMA-co- VNPEGMAA) as component at 1 mg/ml total solid contents in trifluoroethanol. 6-well plates were prepared with this solution as described in EXAMPLE 3 above. The amount of immobilized peptide was quantified by BCA. The results are shown in FIG. 11.

The data obtained from this example shown clearly that blend prepared from Photo-HEMA (not a positively charged photoreactive hydrogel forming copolymer) cannot be used at concentration as low as 1 mg/ml for culture of embryonic stem cells in a chemically-defined medium (see, FIG. 14b), and associated discussion in EXAMPLE 9 below).

Example 8: Culture of Human Mesenchymal Stem Cells

Human Bone marrow mesenchymal stem cells (hBM-MSC) were obtained via Stemcell technologies (MSC-001F). Cells were grown in mesencult-XF medium (Ref #05420) on cultures plates coated with mesencult substrate (ref#05424) following manufacturer recommendations.

For cell adhesion and growth assays in 6-well plates prepared as described in EXAMPLE 3 above, 30-70K cells/well were seeded in mesencult-XF medium and incubated at 37° C. for 6-8 days until cells in control reach 80% confluency. Cells number in each well were measured using MTT assay.

The possibility to release cells with trypsin treatment was evaluated in a second well by incubating the cells for 5 minutes with 1 mL 0.05% trypsin/0.2% EDTA. Trypsin was then neutralized with serum containing medium (IMDM, 10% FBS), the wells were rinsed with PBS and mesencult-XF medium was added to the well. Cell release was evaluated by phase contrast microscopy and then the number of remaining cells was measured using MTT assay. The ratio of remaining cells to total cells can be quantified by comparing the MTT values.

The plates used were (i) MesenCult® coated 6-well plates, (ii) Synthemax™ 6-well plate (Corning, Inc.), (iii) 10% photoHEMA+90% VN-PEG-co-HEMA, 10 mg/ml, ("10/90 photoHEMA/VNPEGMMA") as described in EXAMPLE 6, (iv) 40% photoDMAE+60% VNPEGMAA-co-HEMA ("40/60 photoDMAE/VNPEGMAA") as described in EXAMPLE 3, and (v) 40% photoHEMA+60% VN-PEG-co-HEMA, 10 mg/ml, ("40/60 photoHEMA/VN-PEGMMA") as described in EXAMPLE 8.

Figure 15:
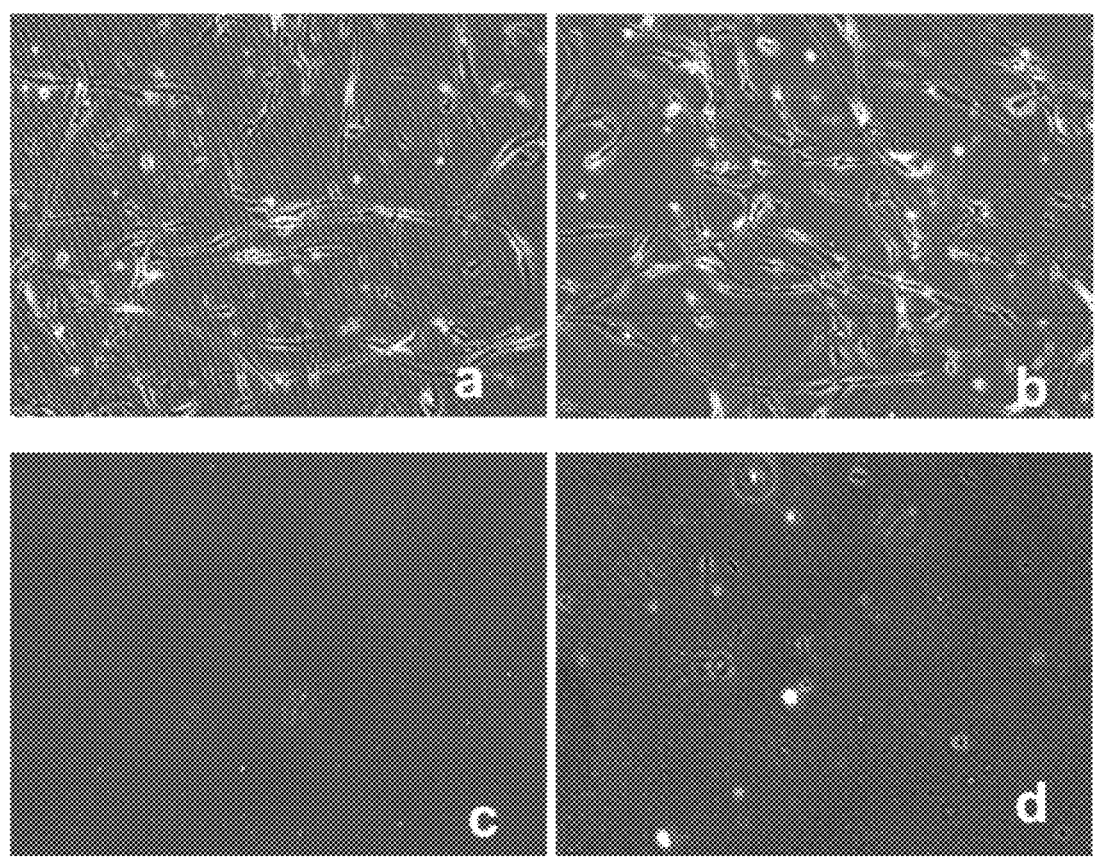
FIGS. 15a-d are phase contrast microscopy images illustrating hBM-MSC morphology grown in mesencult-XF medium, on Mesencult substrate (a) and 40% photoDMAE+ 60% VNPEGMAA-co-HEMA) 1 mg/ml (b). Images c and d illustrate cell release from MesenCult® attachment substrate biological coating (c) and 40% photoDMAE+60% VNPEG-MAA-co-HEMA 1 mg/ml (d) following trypsin treatment.

FIG. 15 shows phase contrast microscopy images of hBM-MSC cells cultured in mesencult-XF medium on MesenCult® substrate (a) and 40/60 photoDMAE/VNPEG-MAA-co-HEMA) (b) and images following tryspin treatment odf hBM-MSC cells cultured in mesencult-XF medium on Mesencult® substrate (c) and 40/60 photoD-MAE/VNPEGMAA-co-HEMA (d). The images presented in (c) and (d) illustrate cell release following trypsin treatment.

Figure 16:
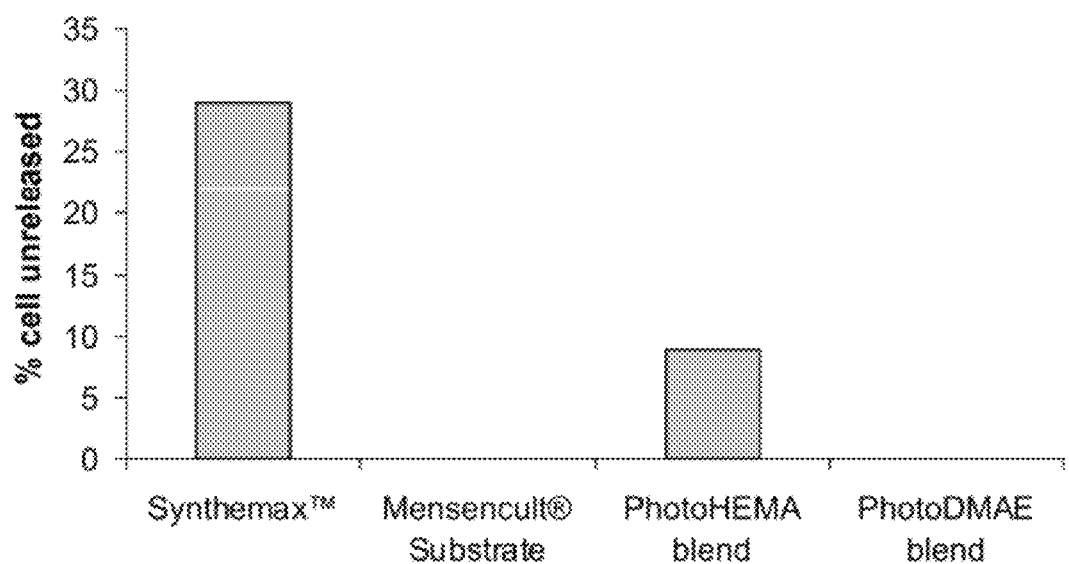
FIG. 16 is a graph showing MTT quantification of the proportion of cells remaining attached to tested surfaces after trypsin treatment.
Figure 18:
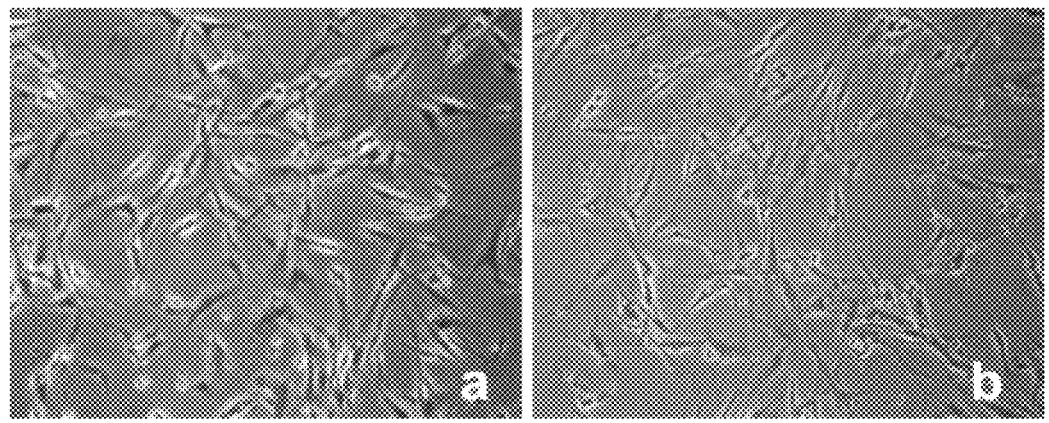
FIGS. 18a-b are phase contrast microscopy images illustrating hBM-MSC morphology grown in Mesencult-XF medium, on MesenCult® attachment substrate biological coating (a) and 40% photoDMAE+60% VNPEGMAA-co-HEMA) 1 mg/ml coated in a CellBIND® CellSTACK™ (b).

FIG. 16 is a graph showing MTT quantification of the proportion of cells remaining attached to the tested surfaces after trypsin treatment for cells cultures on Synthemax™, MesenCult®, 10/90 photoHEMA/VNPEGMMA, and 40/60 photoDMAE/VNPEGMAA-co-HEMA. As shown, cell release is incomplete on the Synthemax™ synthetic surface and on 10/90 photoHEMA/VNPEGMMA, while 40/60 photoDMAE/VNPEGMAA-co-HEMA results in cell harvesting equivalent to MesenCult® attachment substrate biological coating.

hBM-MSC were also cultured in CellBIND® CellSTACK™ culture vessels coated with MesenCult attachment substrate biological coating or 40/60 photo DMAE/VNPEGMMA-Co-HEMA, 1 mg/ml (see EXAMPLE 4 above). FIG. 18 shows phase contrast microscope images of hBM-MSC grown in Mesencult-XF medium, on MesenCult® attachment substrate biological coating (a) and 40/60 photo DMAE/VNPEGMMA-Co-HEMA (b) coated in a CellBIND® CellSTACK™. The images presented in FIG. 18 show similar morphology and coverage of hBM-MSC on both substrates.

Figure 19:
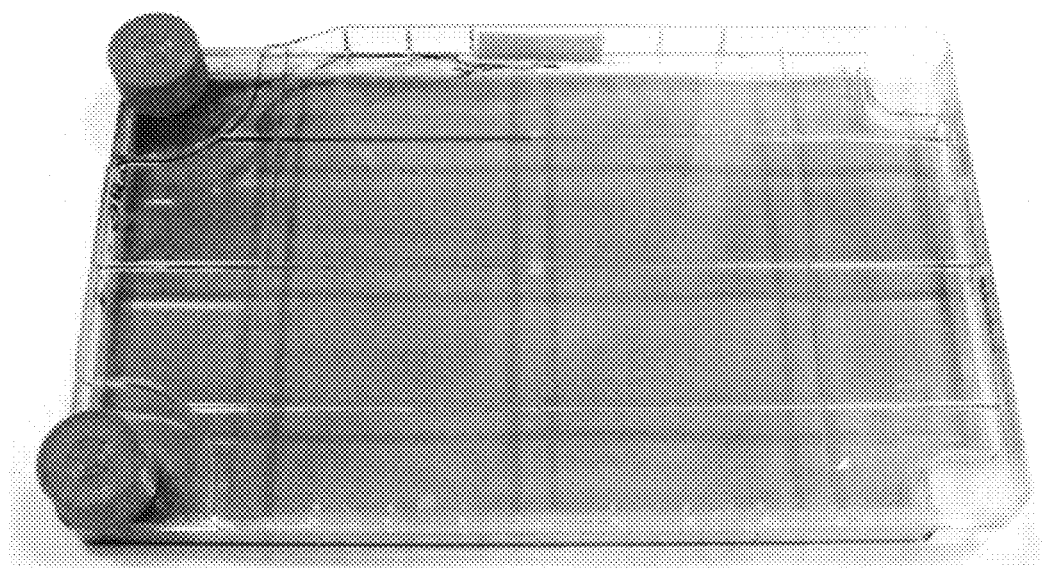
FIG. 19 is a photograph showing crystal violet staining of hBM-MSCcells grown in mesencult-XF medium, on 40% photoDMAE+60% VNPEGMAA-co-HEMA 1 mg/ml, coated in a CellBind® CellSTACK™.

FIG. 19 is photograph showing crystal violet staining of hBM-MSCcells grown in mesencult-XF medium on 40/60 photo DMAE/VNPEGMMA-Co-HEMA, 1 mg/ml, coated in a CellBind® CellSTACK™. This image illustrates the homogeneity of cell adhesion and growth of mesenchymal stem cells in this type of vessel when using a coating described herein.

Example 9: Culture of Mouse Embryonic Stem Cells

ES-D3 cells (ATCC # CRL-11632) were grown in DMEM medium supplemented with 15% FBS and 0.1 mM beta-mercaptoethanol as recommended by ATCC. Cells were trypsinized and diluted before they reach confluency.

For adhesion assays ES-D3 were collected by trypsination, counted, washed in D-PBS and resuspended in mTeSR1 synthetic medium (Stem cell technologies) supplemented with LIF. $7.5 \times 10^5$ cells per well were then seeded in 6-well plate format in 2 mL mTeSR1+LIF and incubated at 37° C. The plates used were (i) Matrigel® coated 6-well plates, (ii) Synthemax™ 6-well plate (Corning, Inc.), (iii) 10% photoHEMA+90% VN-PEG-co-HEMA, 10 mg/ml, ("10/90 photoHEMA/VNPEGMMA") as described in EXAMPLE 6, (iv) 40% photoDMAE+60% VNPEGMAA-co-HEMA ("40/60 photoDMAE/VNPEGMAA") as described in EXAMPLE 3, and (v) 40% photoHEMA+60% VN-PEG-co-HEMA, 10 mg/ml, ("40/60 photoHEMA/VN-PEGMMA") as described in EXAMPLE 8. Cell morphology was examined after 24 hours and representative phase-contrast microscopy photos were taken.

Figure 13:
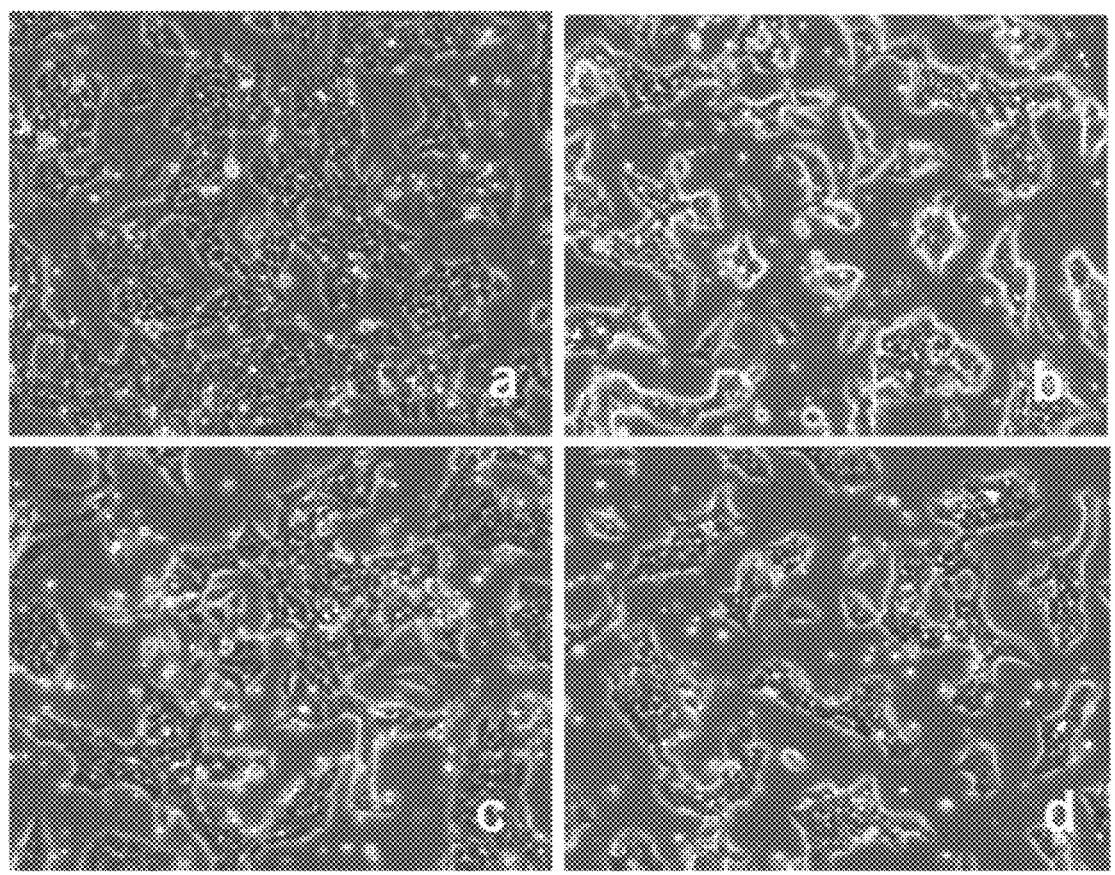
FIGS. 13a-d are a phase contrast microscopy image illustrating ES-D3 mESC morphology after 24 hours of adhesion on Matrigel™ coated 6 well plate (a), Synthemax™ 6 well plate (b), 10% photoHEMA+90% VN-PEG-MAA-co-HEMA, 10 mg/ml (c) and 40% photoDMAE+60% VNPEGMAA-co-HEMA, 1 mg/ml (d).

Some of the resulting photos are presented in FIG. 13, where (a) is Matrigel®, (b) is Synthemax™, (c) is 10/90 photoHEMA/VNPEGMMA, and (d) is 40/60 photoDMAE/VNPEGMAA. All of the substrates supported culture of the ES-D3 cells. However, it is noted that the morphology of the cells cultured on the 40/60 photoDMAE/VNPEGMAA substrate more closely resembled the morphology of cells cultured on Martigel® than the cells cultured on Synthemax™, even though the Synthemax™ substrate had a peptide concentration about 100 times that of the 40/60 photoDMAE/VNPEGMAA substrate.

Figure 14:
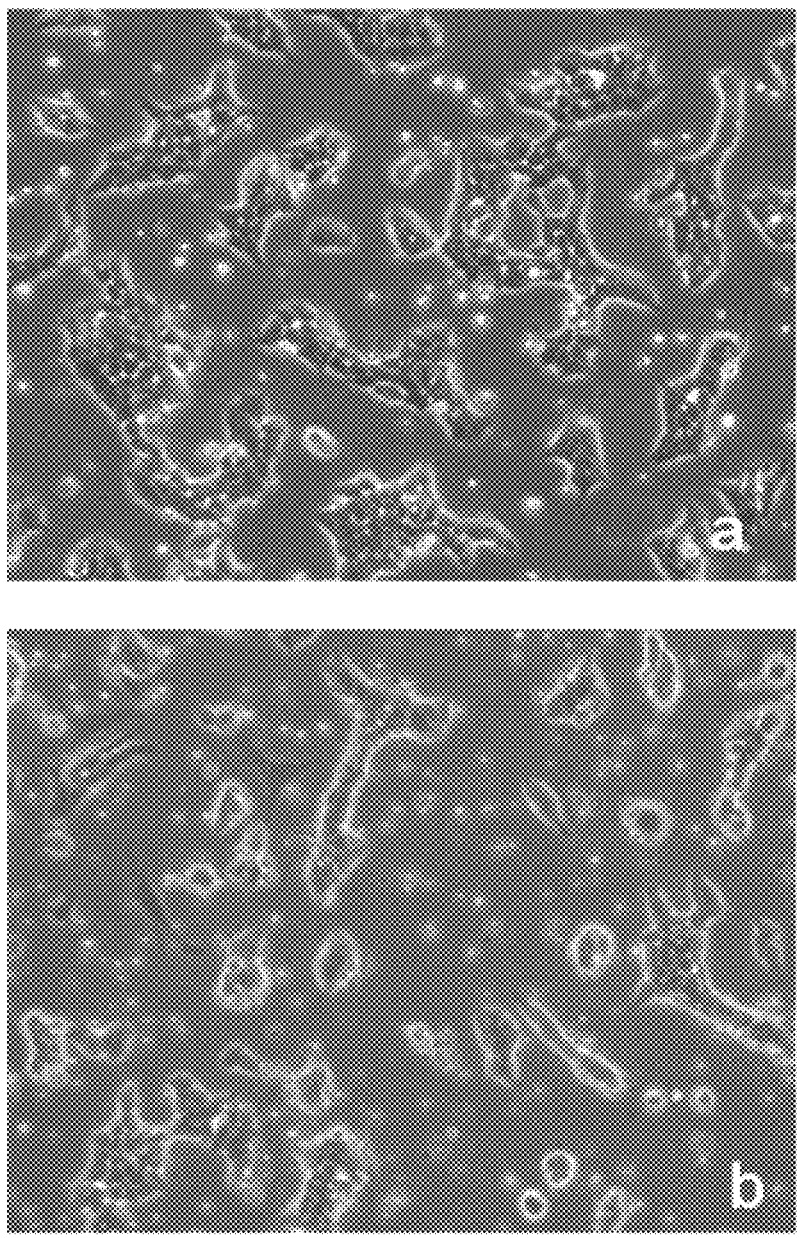
FIGS. 14a-b are a phase contrast microscopy pictures illustrating ES-D3 mESC morphology after 24 hours of adhesion on 40% photoDMAE+60% VNPEGMAA-co-HEMA) 1 mg/ml (a) and 40% photoHEMA+60% VNPEG-MAA-co-HEMA) 1 mg/ml (b).

Some additional photos are presented in FIG. 14, where (a) is 40/60 photoDMAE/VNPEGMAA and (b) is 40/60 photoHEMA/VNPEGMMA. As shown, the 40/60 photoD-MAE/VNPEGMAA supported the culture of the ES-D3 cells, whereas the 40/60 photoHEMA/VNPEGMMA did not. This is somewhat surprising as the concentration of peptide is lower in the 40/60 photoDMAE/VNPEGMAA substrate than in the 40/60 photoHEMA/VNPEGMMA substrate (see FIG. 11).

Thus, embodiments of SYNTHETIC COMPOSITION AND COATING FOR CELL CULTURE are disclosed. One skilled in the art will appreciate that the coatings, articles, compositions and methods described herein can be practiced with embodiments other than those disclosed. The disclosed embodiments are presented for purposes of illustration and not limitation.

What is claimed is:

1. A composition for forming a polymeric cell culture surface comprising:
   a pre-polymer comprising a polymer backbone, an amine cationic moiety conjugated to the backbone wherein the amine cationic moiety results from polymerization of a monoalkylaminoalkyl (meth) acrylate, N-tert-butylaminoethyl (meth)acrylate, or a dialkylaminoalkyl (meth) acrylate monomer selected from the group consisting of N,N-dimethylaminoethyl(meth)acrylate, N—N-diethylaminoethyl (meth) acrylate and N,N-dipropylaminoethyl (meth) acrylate, and a cross-linker moiety conjugated to the backbone; and
   a peptide-polymer comprising a polymer backbone and cell adhesive peptide conjugated to the backbone.

2. The composition of claim 1, wherein the amine cationic moiety conjugated to the polymer backbone results from the polymerization of a monomer into the pre-polymer, wherein the monomer is selected from the group consisting of an N,N-dimethylaminoethyl(meth)acrylate, an N,N-diethylaminoethyl (meth)acrylate, and an N,N-dipropylaminoethyl (meth)acrylate.

3. The composition of claim 1, wherein the amine cationic moiety conjugated to the polymer backbone results from polymerization of a 2-(dimethylamino) ethyl methacrylate (DMEMA) monomer to form the pre-polymer.

4. The composition of claim 1, wherein the pre-polymer further comprises a hydrophilic moiety conjugated to the polymer backbone of the pre-polymer.

5. The composition of claim 4, wherein the hydrophilic moiety conjugated to the polymer backbone results from polymerization of a monomer into the pre-polymer, wherein the monomer is selected from the group consisting of 2-carboxyethyl methacrylate, 2-carboxyethyl acrylate, acrylic acid, methacrylic acid, hydroxypropyl methacrylate, 2-hydroxyethyl methacrylate (HEMA), 2-hydroxyethyl acrylate, glycerol methacrylate, hydroxypropyl acrylate, 4-hydroxybutyl acrylate, 2-carboxyethyl acrylamide, acrylamidoglycolic acid, N-(hydroxymethyl)acrylamide, N-[Tris (hydroxymethyl)methyl]acrylamide, 3-acryloylamino-1-propanol, N-acrylamido-ethoxyethanol, and N-hydroxyethyl acrylamide.

6. The composition of claim 4, wherein the hydrophilic moiety conjugated to the polymer backbone results from polymerization of a 2-hydroxyethyl methacrylate (HEMA) monomer to form the pre-polymer.

7. The composition of claim 1, wherein the cross-linker moiety is a benzophenone moiety.

8. The composition of claim 1, wherein the cell adhesive peptide comprises an R-G-D sequence.

9. The composition of claim 1, wherein the cell adhesive peptide is a sequence of amino acids found in vitronectin, laminin, bone sialoprotein, collagen, or fibronectin.

10. The composition of claim 1, wherein the cell adhesive peptide comprises a sequence of amino acids selected from the group consisting of: KGGGQKCIVQTTSWSQCSKS (SEQ ID NO:1), GGGQKCIVQTTSWSQCSKS (SEQ ID NO:2), KYGLALERKDHSG (SEQ ID NO:3), YGLALERKDHSG (SEQ ID NO:4), KGGSINNNRWHSIYITRFGNMGS (SEQ ID NO:5), GSINNNRWHSIYITRFGNMGS (SEQ ID NO:6), KGGTWYKIAFQRNRK (SEQ ID NO:7), GGTWYKIAFQRNRK (SEQ ID NO:8), KGGTSIKIRGTYSER (SEQ ID NO:9), GGTSIKIRGTYSER (SEQ ID NO:10), KYGTDIRVTLNRLNTF (SEQ ID NO:11), YGTDIRVTLNRLNTF (SEQ ID NO:12), KYGSETTVKYIFRLHE (SEQ ID NO:13), YGSETTVKYIFRLHE (SEQ ID NO:14), KYGKAFDITYVRLKF (SEQ ID NO:15), YGKAFDITYVRLKF (SEQ ID NO:16), KYGAASIKVAVSADR (SEQ ID NO:17), YGAASIKVAVSADR (SEQ ID NO:18), CGGNGEPRGDTYRAY (SEQ ID NO:19), GGNGEPRGDTYRAY (SEQ ID NO:20), CGGNGEPRGDTRAY (SEQ ID NO:21), GGNGEPRGDTRAY (SEQ ID NO:22), KYGRKRLQVQLSIRT (SEQ ID NO:23), YGRKRLQVQLSIRT (SEQ ID NO:24), KGGRNIAEIIKDI (SEQ ID NO:25), GGRNIAEIIKDI (SEQ ID NO:26), KGGPQVTRGDVFTMP (SEQ ID NO:27), GGPQVTRGDVFTMP (SEQ ID NO:28), GRGDSPK (SEQ ID NO:29), KGGAVTGRGDSPASS (SEQ ID NO:30), GGAVTGRGDSPASS (SEQ ID NO:31), $Yaa_1$PQVTRGNVFTMP (SEQ ID NO:32), RGDYK (SEQ ID NO:33), and combinations thereof.

11. The composition of claim 1, wherein the cell adhesive peptide is incorporated into the peptide-polymer from a peptide monomer of the formula $R_m$—$S_p$—$C_{ap}$;

wherein R is a polymerization moiety selected from the group consisting of acrylate, methacrylate, acrylamide, methacrylamide, maleimide and fumarate and any combination thereof, and m is an integer greater than 1;

wherein $S_p$ is an optional spacer moiety wherein the spacer moiety comprises polyethylene oxide or polypropylene oxide having the formula $(O-CH_2CHR')_{m2}$ where R' is H or $CH_3$ and m2 is an integer from 0 to 20, or $Xaa_n$ wherein Xaa is independently any amino acid and n is an integer from 0 to 20, or any combination thereof; and, wherein $C_{ap}$ is a peptide comprising an R-G-D sequence.

12. The composition of claim 1, wherein the peptide-polymer further comprises a hydrophilic moiety conjugated to the backbone of the peptide-polymer.

13. The composition of claim 12, wherein the hydrophilic moiety conjugated to the polymer backbone results from polymerization of a monomer into the pre-polymer, wherein the monomer is selected from the group consisting of 2-carboxyethyl methacrylate, 2-carboxyethyl acrylate, acrylic acid, methacrylic acid, hydroxypropyl methacrylate, 2-hydroxyethyl methacrylate (HEMA), 2-hydroxyethyl acrylate, glycerol methacrylate, hydroxypropyl acrylate, 4-hydroxybutyl acrylate, 2-carboxyethyl acrylamide, acrylamidoglycolic acid, N-(hydroxymethyl)acrylamide, N-[Tris(hydroxymethyl)methyl]acrylamide, 3-acryloylamino-1-propanol, N-acrylamido-ethoxyethanol, and N-hydroxyethyl acrylamide.

14. The composition of claim 1, wherein the peptide-polymer comprises the polymerization product of an ethylenically unsaturated monomer having a carboxyl group with an ethylenically unsaturated monomer not having a carboxyl group, wherein the cell adhesive peptide is conjugated to the pre-polymer via the carboxyl group, and wherein the ethylenically unsaturated monomer not having the carboxyl group is hydrophilic.

15. A method of making a cell culture article comprising providing the pre-polymer and peptide-polymer of claim 1 to a substrate and exposing the pre-polymer and peptide-polymer on the substrate to an energy source to cross-link the pre-polymer and peptide-polymer to each other and to the substrate.

16. A cell culture article made by the method of claim 15.

* * * * *

SEQUENCE LISTING

<160> NUMBER OF SEQ ID NOS: 33

<210> SEQ ID NO 1
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 1

Lys Gly Gly Gly Gln Lys Cys Ile Val Gln Thr Thr Ser Trp Ser Gln
1               5                   10                  15

Cys Ser Lys Ser
            20

<210> SEQ ID NO 2
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 2

Gly Gly Gly Gln Lys Cys Ile Val Gln Thr Thr Ser Trp Ser Gln Cys
1               5                   10                  15

Ser Lys Ser

<210> SEQ ID NO 3
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 3

Lys Tyr Gly Leu Ala Leu Glu Arg Lys Asp His Ser Gly
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 4

Tyr Gly Leu Ala Leu Glu Arg Lys Asp His Ser Gly
1               5                   10

<210> SEQ ID NO 5
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 5

Lys Gly Gly Ser Ile Asn Asn Asn Arg Trp His Ser Ile Tyr Ile Thr
1               5                   10                  15

Arg Phe Gly Asn Met Gly Ser
            20

<210> SEQ ID NO 6
<211> LENGTH: 22
<212> TYPE: PRT

<213> ORGANISM: Artificial Sequence
<220> FEATURE:
<223> OTHER INFORMATION: Synthetic polypeptide

<400> SEQUENCE: 6

Gly Gly Ser Ile Asn Asn Asn Arg Trp His Ser Ile Tyr Ile Thr Arg
1               5                   10                  15

Phe Gly Asn Met Gly Ser
            20

<210> SEQ ID NO 7
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 7

Lys Gly Gly Thr Trp Tyr Lys Ile Ala Phe Gln Arg Asn Arg Lys
1               5                   10                  15

<210> SEQ ID NO 8
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 8

Gly Gly Thr Trp Tyr Lys Ile Ala Phe Gln Arg Asn Arg Lys
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 9

Lys Gly Gly Thr Ser Ile Lys Ile Arg Gly Thr Tyr Ser Glu Arg
1               5                   10                  15

<210> SEQ ID NO 10
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 10

Gly Gly Thr Ser Ile Lys Ile Arg Gly Thr Tyr Ser Glu Arg
1               5                   10

<210> SEQ ID NO 11
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 11

Lys Tyr Gly Thr Asp Ile Arg Val Thr Leu Asn Arg Leu Asn Thr Phe
1               5                   10                  15

<210> SEQ ID NO 12

<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 12

Tyr Gly Thr Asp Ile Arg Val Thr Leu Asn Arg Leu Asn Thr Phe
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 13

Lys Tyr Gly Ser Glu Thr Thr Val Lys Tyr Ile Phe Arg Leu His Glu
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 14

Tyr Gly Ser Glu Thr Thr Val Lys Tyr Ile Phe Arg Leu His Glu
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 15

Lys Tyr Gly Lys Ala Phe Asp Ile Thr Tyr Val Arg Leu Lys Phe
1               5                   10                  15

<210> SEQ ID NO 16
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 16

Tyr Gly Lys Ala Phe Asp Ile Thr Tyr Val Arg Leu Lys Phe
1               5                   10

<210> SEQ ID NO 17
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 17

Lys Tyr Gly Ala Ala Ser Ile Lys Val Ala Val Ser Ala Asp Arg
1               5                   10                  15

<210> SEQ ID NO 18
<211> LENGTH: 14

```
<212> TYPE: PRT
<213> ORGANISM: Artificial Sequence
<220> FEATURE:
<223> OTHER INFORMATION: Synthetic polypeptide

<400> SEQUENCE: 18

Tyr Gly Ala Ala Ser Ile Lys Val Ala Val Ser Ala Asp Arg
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 19

Cys Gly Gly Asn Gly Glu Pro Arg Gly Asp Thr Tyr Arg Ala Tyr
1               5                   10                  15

<210> SEQ ID NO 20
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 20

Gly Gly Asn Gly Glu Pro Arg Gly Asp Thr Tyr Arg Ala Tyr
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 21

Cys Gly Gly Asn Gly Glu Pro Arg Gly Asp Thr Arg Ala Tyr
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 22

Gly Gly Asn Gly Glu Pro Arg Gly Asp Thr Arg Ala Tyr
1               5                   10

<210> SEQ ID NO 23
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 23

Lys Tyr Gly Arg Lys Arg Leu Gln Val Gln Leu Ser Ile Arg Thr
1               5                   10                  15

<210> SEQ ID NO 24
<211> LENGTH: 14
<212> TYPE: PRT
```

<213> ORGANISM: Artificial Sequence
<220> FEATURE:
<223> OTHER INFORMATION: Synthetic polypeptide

<400> SEQUENCE: 24

Tyr Gly Arg Lys Arg Leu Gln Val Gln Leu Ser Ile Arg Thr
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 25

Lys Gly Gly Arg Asn Ile Ala Glu Ile Ile Lys Asp Ile
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 26

Gly Gly Arg Asn Ile Ala Glu Ile Ile Lys Asp Ile
1               5                   10

<210> SEQ ID NO 27
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 27

Lys Gly Gly Pro Gln Val Thr Arg Gly Asp Val Phe Thr Met Pro
1               5                   10                  15

<210> SEQ ID NO 28
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 28

Gly Gly Pro Gln Val Thr Arg Gly Asp Val Phe Thr Met Pro
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 29

Gly Arg Gly Asp Ser Pro Lys
1               5

<210> SEQ ID NO 30
<211> LENGTH: 15
<212> TYPE: PRT
<213> ORGANISM: Artificial Sequence

```
<220> FEATURE:
<223> OTHER INFORMATION: Synthetic polypeptide

<400> SEQUENCE: 30

Lys Gly Gly Ala Val Thr Gly Arg Gly Asp Ser Pro Ala Ser Ser
1               5                   10                  15

<210> SEQ ID NO 31
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 31

Gly Gly Ala Val Thr Gly Arg Gly Asp Ser Pro Ala Ser Ser
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Xaa
<222> LOCATION: (1)..(1)
<223> OTHER INFORMATION: Xaa = any amino acid

<400> SEQUENCE: 32

Xaa Pro Gln Val Thr Arg Gly Asp Val Phe Thr Met Pro
1               5                   10

<210> SEQ ID NO 33
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 33

Arg Gly Asp Tyr Lys
1               5
```